(12) United States Patent
Eggert et al.

(10) Patent No.: US 11,648,117 B2
(45) Date of Patent: May 16, 2023

(54) DEVICES, SYSTEMS, AND METHODS FOR CLAMPING A LEAFLET OF A HEART VALVE

(71) Applicant: Boston Scientific Scimed, Inc., Maple Grove, MN (US)

(72) Inventors: Joel T. Eggert, Plymouth, MN (US); Aaron Abbott, Columbia Hieghts, MN (US); Daniel Shuey, Pine City, MN (US); James P. Rohl, Prescott, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 175 days.

(21) Appl. No.: 16/919,782

(22) Filed: Jul. 2, 2020

(65) Prior Publication Data

US 2021/0007847 A1 Jan. 14, 2021

Related U.S. Application Data

(60) Provisional application No. 62/873,354, filed on Jul. 12, 2019.

(51) Int. Cl.
*A61F 2/24* (2006.01)

(52) U.S. Cl.
CPC .... *A61F 2/2457* (2013.01); *A61F 2220/0016* (2013.01)

(58) Field of Classification Search
CPC ... A61F 2/2457; A61F 2/2487; A61B 17/0644
See application file for complete search history.

(56) References Cited

U.S. PATENT DOCUMENTS

| 5,156,609 A | 10/1992 | Nakao et al. |
| 7,736,388 B2 | 6/2010 | Goldfarb et al. |

(Continued)

FOREIGN PATENT DOCUMENTS

| CN | 202798013 U | 3/2013 |
| FR | 3063631 A1 | 9/2018 |
| WO | 2008112237 A2 | 9/2008 |

OTHER PUBLICATIONS

International Search Report and Written Opinion for the International Patent Application No. PCT/US2020/040673, dated Jan. 18, 2021, 20 pages.

*Primary Examiner* — Suba Ganesan
(74) *Attorney, Agent, or Firm* — Seager, Tufte & Wickhem LLP

(57) ABSTRACT

The present disclosure relates generally to the field of medical devices for clamping a leaflet of a heart valve. In particular, the present disclosure relates to medical devices, systems, and methods for delivering artificial chordae tendineae in a patient. In an embodiment, a system may include a clamp having a plurality of arms at a first end. The plurality of arms may have a closed configuration in which the arms are oriented toward each other, and an open configuration in which the arms are oriented away from each other. A spring portion may be coupled to the plurality of arms at a second end that is configured to bias the arms to the closed configuration. The arms of the clamp may be configured to fixedly engage with a leaflet of the heart valve. The second end of the clamp may be configured to couple to an artificial chordae tendineae.

15 Claims, 21 Drawing Sheets

(56) References Cited

U.S. PATENT DOCUMENTS

| | | |
|---|---|---|
| 8,252,050 B2 | 8/2012 | Maisano et al. |
| 9,622,862 B2 | 4/2017 | Lashinski et al. |
| 9,681,864 B1 | 6/2017 | Gammie et al. |
| 9,848,983 B2 | 12/2017 | Lashinski et al. |
| 10,136,993 B1 | 11/2018 | Metchik et al. |
| 10,258,466 B2 | 4/2019 | Lashinski et al. |
| 2005/0116023 A1 | 6/2005 | Amundson et al. |
| 2007/0118151 A1 | 5/2007 | Davidson |
| 2009/0105729 A1 | 4/2009 | Zentgraf |
| 2010/0161042 A1 | 6/2010 | Maisano et al. |
| 2011/0060407 A1 | 3/2011 | Ketai et al. |
| 2015/0250590 A1 | 9/2015 | Gries et al. |
| 2016/0158008 A1* | 6/2016 | Miller .................. A61F 2/2487 623/2.11 |
| 2017/0252032 A1 | 9/2017 | Hiorth et al. |
| 2018/0185153 A1 | 7/2018 | Bishop et al. |
| 2018/0303614 A1 | 10/2018 | Schaffner et al. |
| 2020/0085577 A1* | 3/2020 | Vola ..................... A61F 2/2457 |

\* cited by examiner

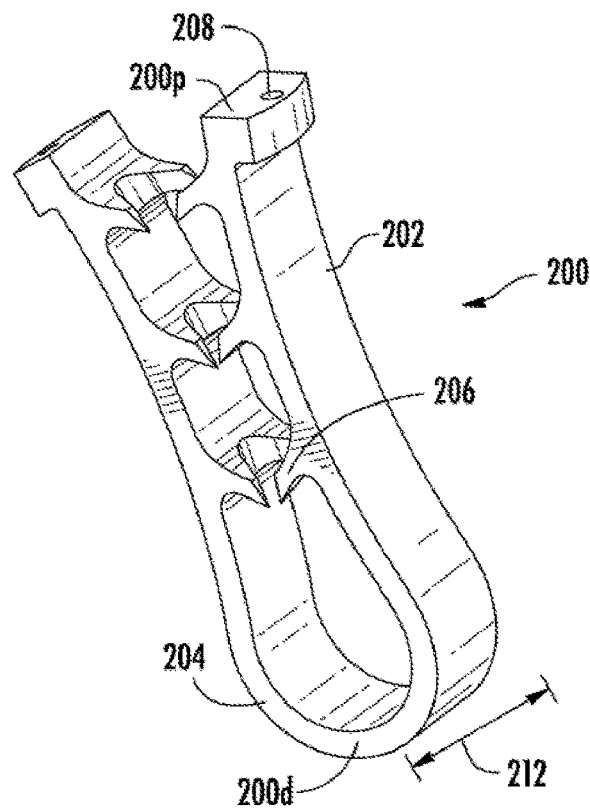
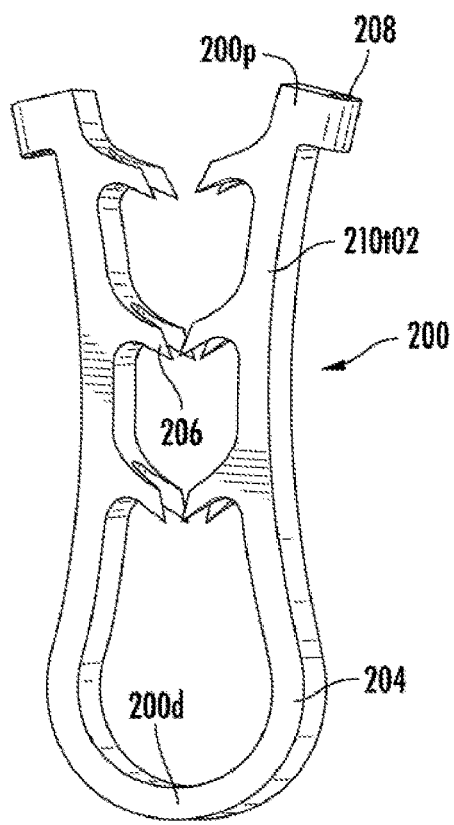
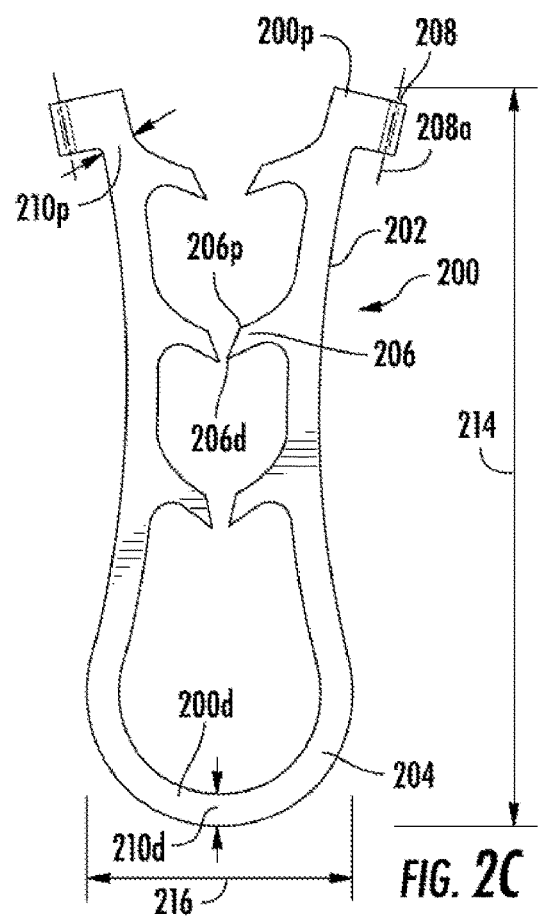
FIG. 2A
FIG. 2B
FIG. 2C

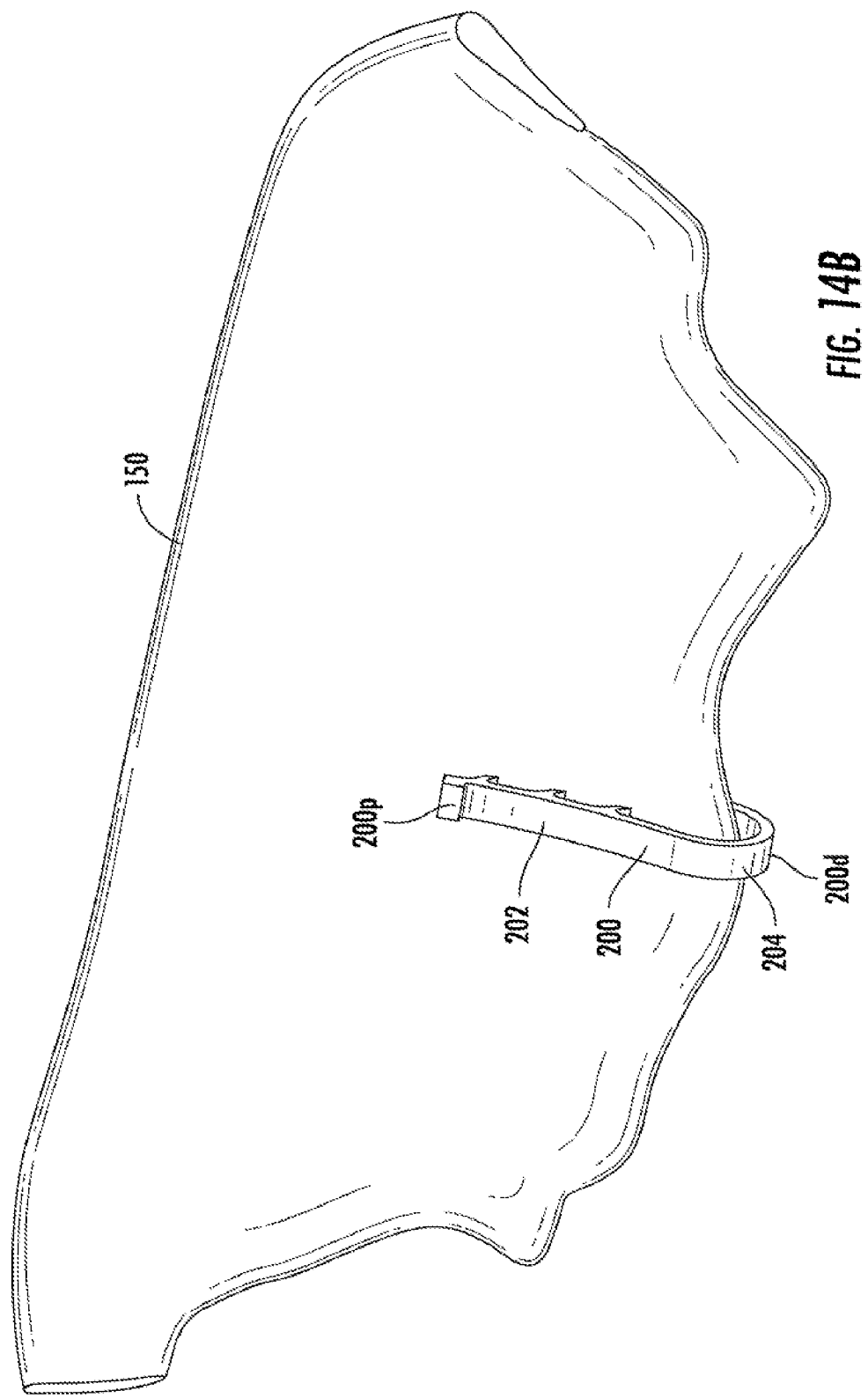

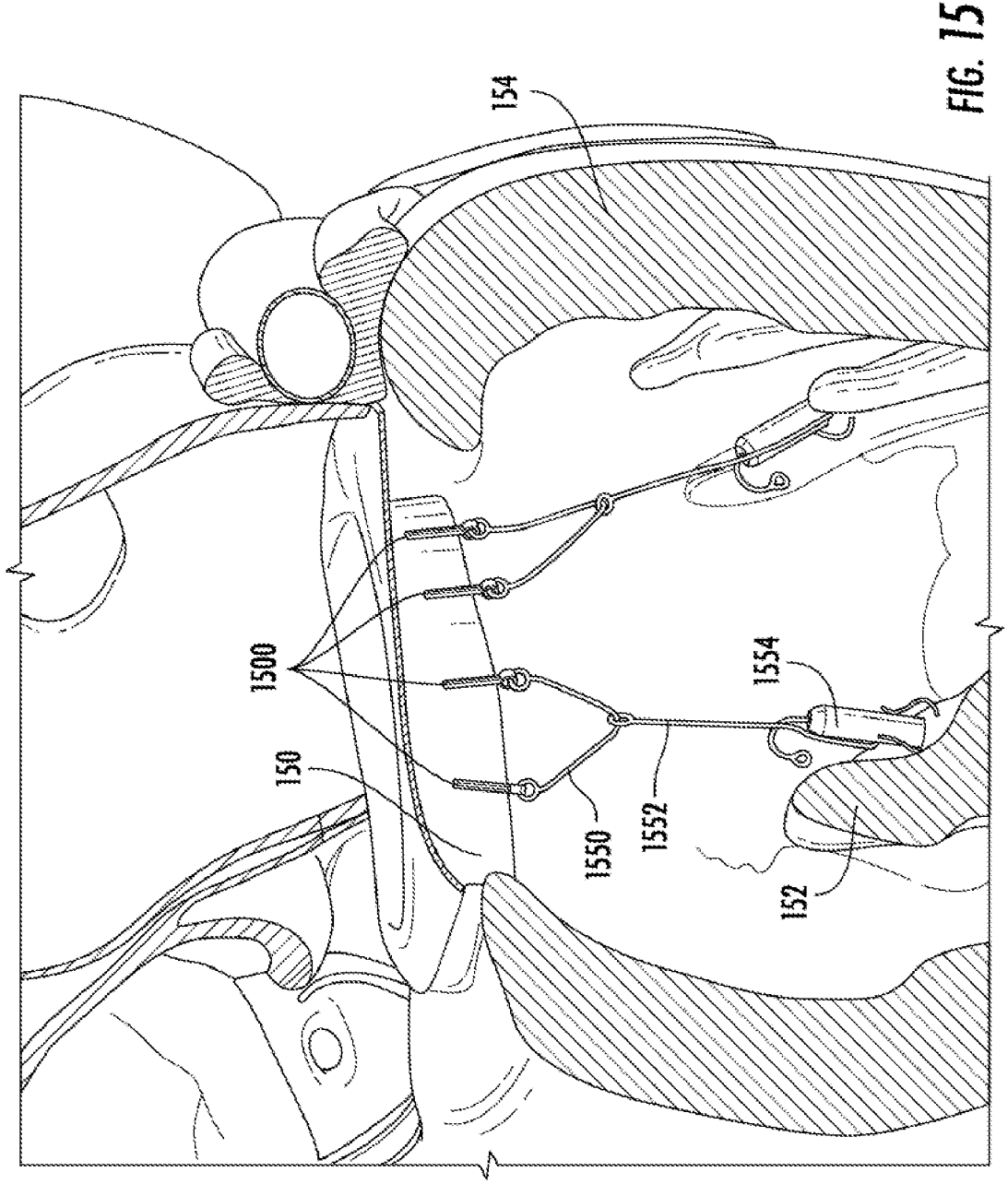

DEVICES, SYSTEMS, AND METHODS FOR CLAMPING A LEAFLET OF A HEART VALVE

CROSS-REFERENCE TO RELATED APPLICATION

The present application claims the benefit of priority under 35 U.S.C. § 119 to U.S. Provisional Patent Application 62/873,354, filed Jul. 12, 2019, which application is incorporated herein by reference in its entirety for all purposes.

FIELD

The present disclosure relates generally to the field of medical devices for clamping a leaflet of a heart valve. In particular, the present disclosure relates to medical devices, systems and methods for delivering artificial chordae tendineae in a patient.

BACKGROUND

Mitral valve disease is typically repaired via invasive surgical intervention or by complicated pinching of the leaflets together creating dual, smaller openings, or a mitral valve replacement of the native valve. These approaches involve risky by-pass surgery that may include an opening into the patient's chest and heart chamber to expose the mitral valve for direct viewing and repair. Resection, partial removal, and/or repair of the patient's leaflets along with the implantation of a surgical ring are complex techniques used by surgeons to reduce the diameter of the patient's mitral annulus, thus allowing the leaflets to properly coapt and reduce mitral regurgitate flow. Some techniques may slightly reduce regurgitate flow but may not provide a durable solution and do not repair and/or replace damaged chordae tendineae of a valve. Thus, transluminal solutions to mitral valve disease are needed.

A variety of advantageous medical outcomes may be realized by the medical devices, systems, and methods of the present disclosure, which include clamping of a leaflet of a heart valve.

SUMMARY

Embodiments of the present disclosure may assist generally with clamping of a heart valve and providing a connection point for a filament. In one aspect, a system for clamping a leaflet of a heart valve may include a clamp. The clamp may include a plurality of arms at a first end. The plurality of arms may have a closed configuration in which the arms are oriented toward each other, and an open configuration in which the arms are oriented away from each other at an open distance between the arms that is greater than a closed distance between the arms in the closed configuration. The closed distance may be zero millimeters. A spring portion may be coupled to the plurality of arms at a second end. The spring portion may be configured to bias the arms to the closed configuration. The arms of the clamp may be configured to fixedly engage with a leaflet of the heart valve. The second end of the clamp may be configured to couple to an artificial chordae tendineae.

In various embodiments described here or otherwise, a spreader may be configured to transition the clamp between the closed configuration and the open configuration. The spreader may include a base. A pin may extend from the base. A lever may be rotatably disposed about the pin. A first channel may extend through the base substantially parallel with a first aperture of one of the plurality of arms and may be configured to accept one of the plurality of arms. A second channel may extend through the lever substantially parallel with a second aperture of one of the plurality of arms and may be configured to accept one of the plurality of arms. A first filament may extend from the lever. The filament may be configured to move the lever and the clamp between the closed configuration and the open configuration. A catheter may have a distal end of the catheter coupled to the base. A first pin may be disposed within the first aperture and the first channel. A second pin may be disposed within the second aperture and the second channel. A second filament may couple the first pin to the second pin. One or more protrusions may be disposed on one or more of the plurality of arms. The one or more protrusions may be selected from the group consisting of barbs, spikes, hooks, and tines. The one or more protrusions may be a plurality of protrusions arranged in columns extending along at least one of the plurality of arms such that the plurality of protrusions are in different planes. The protrusions may extend not more than 50% through a thickness of a wall of the leaflet, e.g., the protrusions may not extend into the wall of a leaflet and may instead distort the tissue. The protrusions may extend a distance from an arm that may be about 0.5 millimeters to about 1.5 millimeters. The clamp may weigh less than 0.08 grams.

In an aspect, a clamp for clamping a leaflet of a heart valve may include a body. The body may include a plurality of arms at a first end. The plurality of arms may have a closed configuration in which the arms are oriented toward each other, and an open configuration in which the arms are oriented away from each other. The arms of the clamp may be configured to fixedly engage with a leaflet of the heart valve. A second end of the clamp may be configured to couple to an artificial chordae tendineae.

In various embodiments described here or otherwise, the body may include a coiled spring portion at a second end. The spring portion may be configured to bias the arms to the closed configuration. A longitudinal axis may extend through the first end and the second end. The clamp may include a first cover disposed adjacent to a first arm of the plurality of arms and extending along the first arm to the longitudinal axis. A second cover may be disposed adjacent to a second arm of the plurality of arms and extending along the second arm to the longitudinal axis. A pin may extend through the first cover, the second cover, and the coiled spring portion. A first channel may be disposed on the first cover having a central axis that is substantially parallel with the first arm. A second channel may be disposed on the second cover having a central axis that is substantially parallel with the second arm. The first and second channels may be configured to substantially align with second and third apertures of a spreader. A first pin may extend into the first channel and the second aperture. A second pin may extend through the second channel and the third aperture. A filament coupling the first pin to the second pin. A tab may be configured to transition the arms between the open configuration and the closed configuration. The open configuration and the closed configuration are may each be stable configurations.

In an aspect, a method of clamping a leaflet of a heart valve may include inserting a catheter through the valve. The catheter may include a spreader disposed on a distal end of the catheter and reversibly coupled to a clamp. The clamp and spreader may be positioned proximate to the leaflet.

Tension on a first filament extending through the catheter may be released and connected to the spreader such that the clamp transitions to a closed configuration about the leaflet. A plurality of pins may be removed from the spreader and clamp such that the spreader releases the clamp. Tension may be applied to the first filament such that the spreader transitions the clamp from the closed configuration to an open configuration. The clamp may be repositioned about the leaflet. Tension may be released on the first filament extending through the catheter such that the clamp transitions to the closed configuration about the leaflet. An artificial chordae tendineae attached to the clamp may be anchored to a papillary muscle. The leaflet may be a flailing leaflet.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 2A illustrates a perspective view of a clamp in a closed configuration, according to an embodiment of the present disclosure.

FIG. 2B illustrates another perspective view of the clamp in FIG. 2A.

FIG. 2C illustrates a side view of the clamp in FIGS. 2A and 2B.

FIG. 14B illustrates another cross-sectional view of the clamp and leaflet of FIG. 14A.

FIG. 15 illustrates a cross-sectional view of a system for clamping a leaflet, according to an embodiment of the present disclosure.

DETAILED DESCRIPTION

Figure 1:
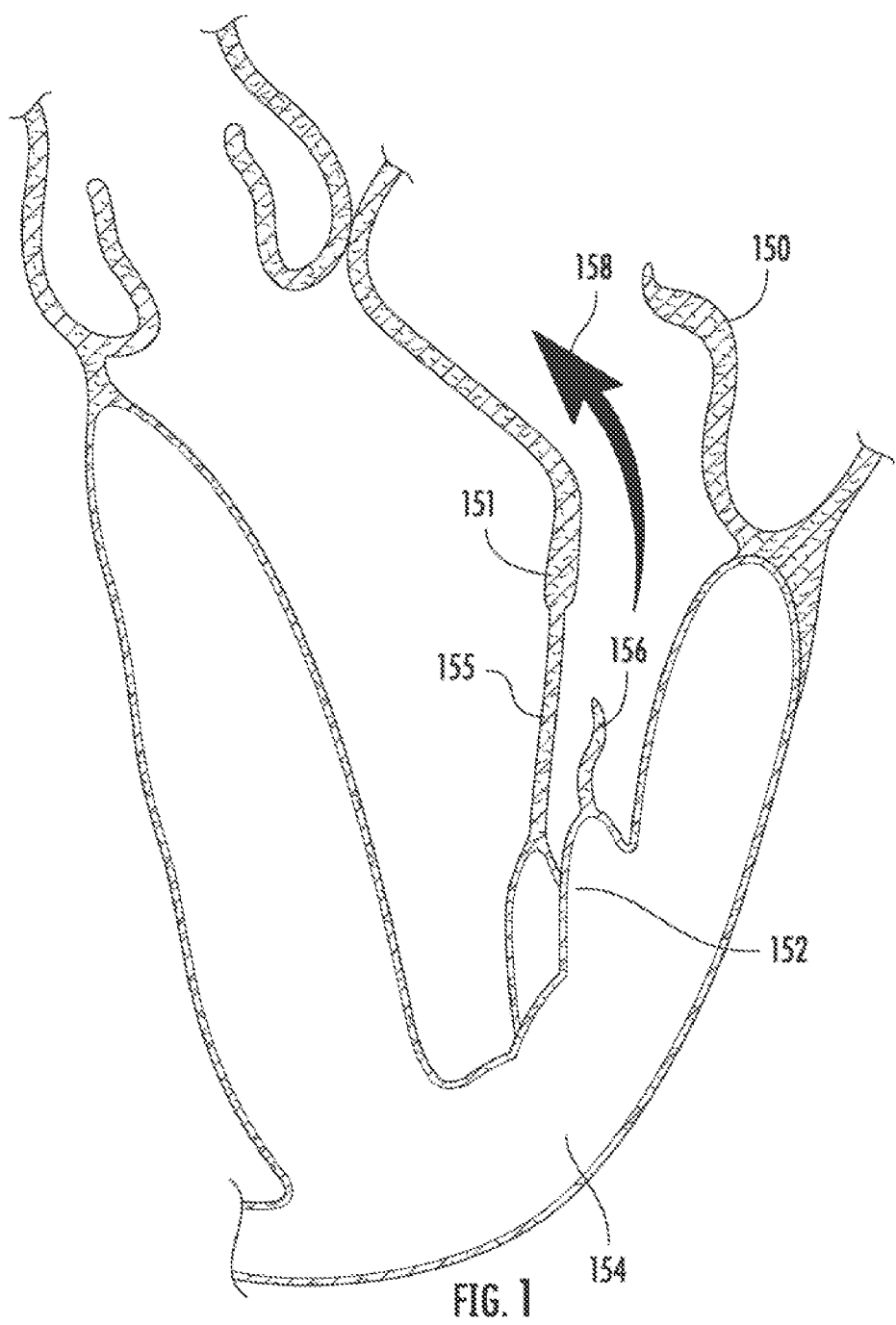
FIG. 1 illustrates a cross-sectional view of flailing leaflet of a mitral valve during blood flow regurgitation.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., transluminal devices inserted through a femoral vein or the like) for selective access to a heart valve, it should be appreciated that such medical devices and systems may be used in a variety of medical procedures that require clamping a leaflet of a valve or clamping a tissue wall. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Heart disease including atrioventricular heart valve malfunctions impede patient cardiac output, which reduces patient quality of life and lifespan. With reference to the heart 154 illustrated in FIG. 1, as heart disease progresses, the chordae tendineae 155 that connect the papillary muscle 152 to a valve leaflet 151 may stretch inelastically and may rupture. A stretched and/or ruptured chordae tendineae 156 may result in a flailing leaflet 150 that may no longer have capacity to form a valving seal for normal heart function. For example, abnormal blood flow regurgitation in the direction of vector 158 may develop. Regurgitation prevents an adequate supply of blood to be delivered through the cardiovascular systems.

Repositioning, repair, and/or replacement of one or more leaflets of a valve and/or chordae tendineae may be desirable to treat heart disease. The devices, systems, and methods of the present disclosure may be used alone or together with other devices, systems, and methods to treat heart disease. Examples of devices, systems, and methods with which embodiments of the present disclosure may be implemented include, but are not limited to, those described in U.S. patent application Ser. No. 16/919,769, filed Jul. 2, 2020, and titled Devices, Systems, and Methods for Adjustably Tensioning an Artificial Chordae Tendineae Between a Leaflet and a Papillary Muscle or Heart Wall; U.S. patent application Ser. No. 16/919,806, filed Jul. 2, 2020, and titled Devices, Systems, and Methods for Artificial Chordae Tendineae; and U.S. patent application Ser. No. 16/919,794, filed Jul. 2, 2020, and titled Devices, Systems, and Methods for Anchoring an Artificial Chordae Tendineae to a Papillary Muscle or Heart Wall, each of which is filed on even date herewith and each of which is herein incorporated by reference in its entirety and for all purposes. Examples of devices described therein may be modified to incorporate embodiments or one or more features of the present disclosure.

Repositioning, repair, and/or replacement of one or more leaflets of a valve and/or chordae tendineae may include one or more devices to be fixed to one or more leaflets of a valve. Embodiments of devices described herein may be fixed to a valve by clamping to a leaflet. These devices may provide a fixed point for other devices, systems, or tools to grab or attach to in order to manipulate a leaflet of a valve and/or deliver devices attached to the leaflet.

Figure 2E:
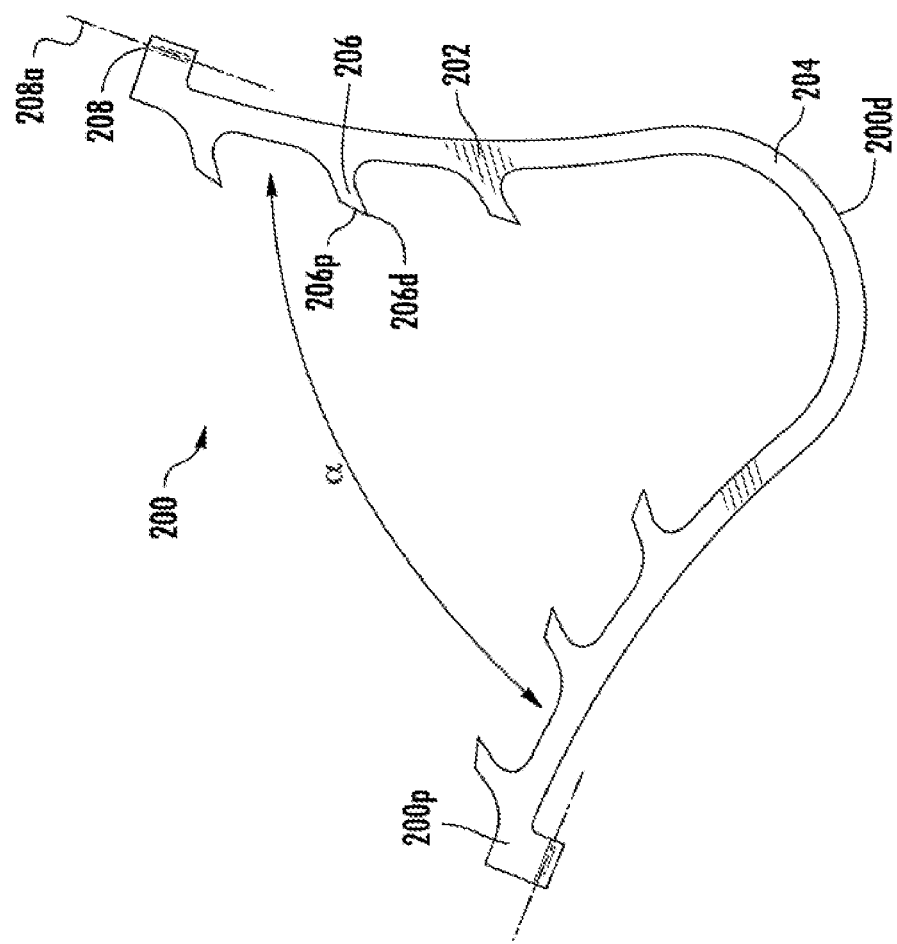
FIG. 2E illustrates a side view of the clamp in FIGS. 2A-2D.
Figure 2D:
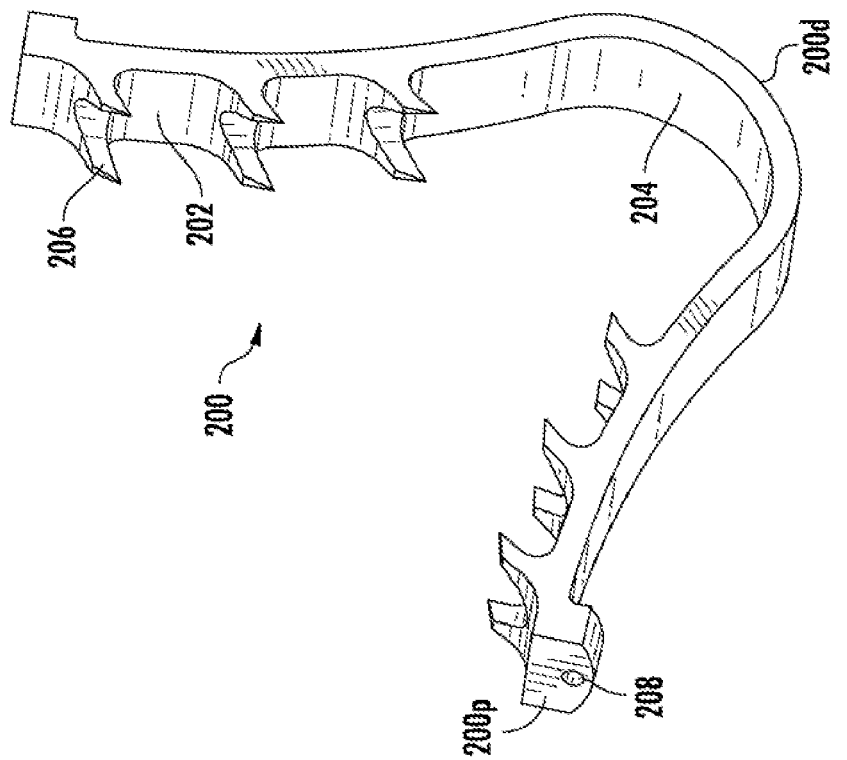
FIG. 2D illustrates a perspective view of the clamp in FIGS. 2A-2C in an open configuration.

With reference to FIGS. 2A-2E, an embodiment of a clamp 200 for clamping a leaflet of a heart valve according to the present disclosure is illustrated, which includes two arms 202 at a first end 200$p$ of the clamp 200. The arms 202 are in the closed configuration in FIGS. 2A-2C in which the arms 202 are oriented toward each other. A spring portion 204 may be at a second end 200$d$ of the clamp 200. The spring portion 204 may be configured to bias the arms 202 to the closed configuration. The spring portion 204 at the second end 200$d$ is wider than a width of the clamp 200 at the location of the arms 202 to reduce stress on the clamp 200 while transitioning between the closed configuration and an open configuration. Each of the arms 202 has an aperture 208 at an end of each arm 202. Each aperture 208 has a central axis 208$a$ that extends substantially along each of the arms 202 and is configured to accept a locking pin for manipulating the clamp 200 between the closed configuration and the open configuration (as will be discussed below with respect to the discussion of FIGS. 13A-15). Each arm 202 includes protrusions 206 that extend along each arm 202 that are configured to embed into tissue. Each of the protrusions has a smooth surface 206$p$ toward the first end 200$p$ of the clamp 200 that is configured to accept a tissue moving between the arms 202 from the first end 200$p$ toward the second end 200$d$. Each protrusion 206 also includes an engaging end 206$d$ toward the second end 200$d$ that is configured to embed into a tissue between the arms 202. Because the engaging end 206$d$ of each protrusion 206 may be angled toward the second end 200$d$ of the clamp 200, the protrusions 206 may resist a movement of a tissue between the arms 202 with respect to the clamp 200 by embedding the engaging ends 206$d$ into the tissue and/or providing a frictional force to the tissue. FIGS. 2D and 2E illustrate the clamp 200 in the open configuration, in which the arms 202 are oriented away from each other. The open configuration can more easily accept tissue (e.g., a leaflet) and can be more easily repositioned to clamp tissue than the closed configuration. The open configuration has the arms 202 apart from each other about an arc length a that may be a various amount of degrees, e.g., about 50°, about 60°, about 90°, etc. The arc length a may be sufficient to enable the clamp 200 to surround at least a portion of a tissue of a valve. A first thickness 210$p$ of the first end 200$p$ of the clamp may be substantially equivalent to a second thickness 210$d$ of the second end 200$d$. Alternatively, the first thickness 210$p$ may be different than the second thickness 210$d$ and this difference in thicknesses may gradually change from the first thickness 210$p$ to the second thickness 210$d$. For example, the first thickness 210$p$ may be thinner than the second thickness 210$d$ or vice versa. For example, one or more thickness 210$p$, 210$d$ of the clamp may be about 0.1 mm to about 3.0 mm such as a first thickness 210$p$ of about 0.7 mm and a second thickness 210$d$ of about 0.1 mm to about 3.0 mm. A width 212 of a clamp may be substantially uniform or may vary along the clamp and may be, e.g., about 2 mm to about 20 mm. A length 214 of a clamp may be, e.g., about 5 mm to about 20 mm. A height 216 of a clamp may be, e.g., about 0.7 mm to about 10 mm.

In various embodiments of the present disclosure, one or more arms of a clamp may have locking features for use with a device that may transition the clamp between a closed configuration and an open configuration. The locking features may include apertures, edges for channels, tabs, or the like. These locking features may be engaged by additional devices such as locking pins, channels, clamps, or the like. The additional devices may engage the locking features to transition the clamp between the closed and open configurations and the additional devices may disengage the locking features to deliver the clamp from one or more devices into a patient.

Figure 3A:
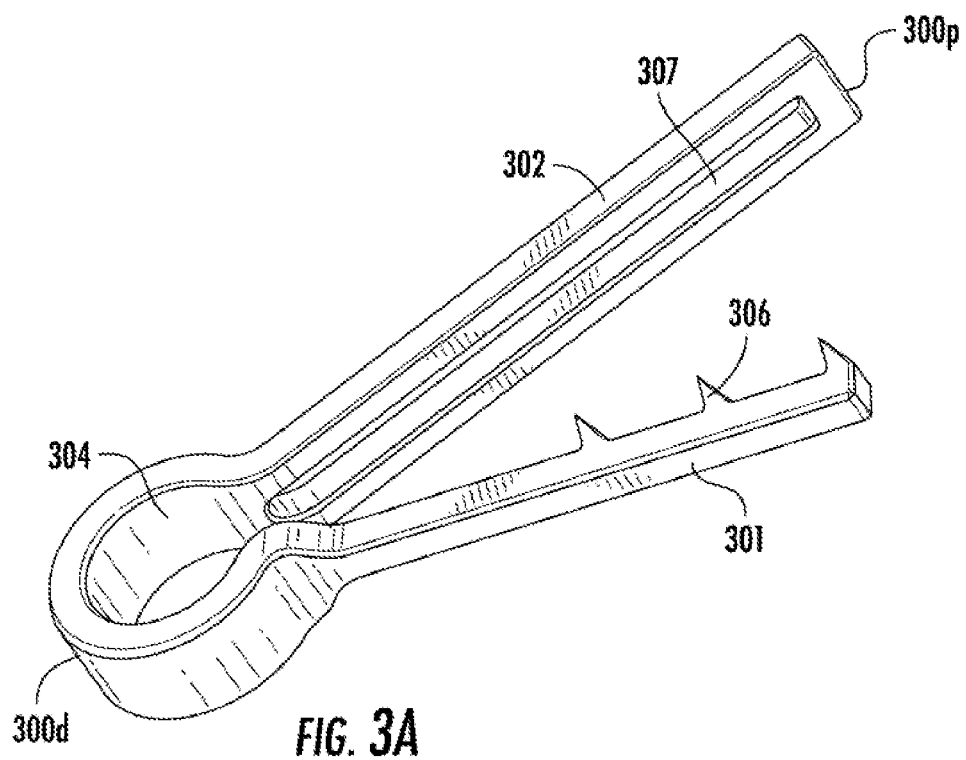
FIG. 3A illustrates a perspective view of a clamp, according to an embodiment of the present disclosure.
Figure 3B:
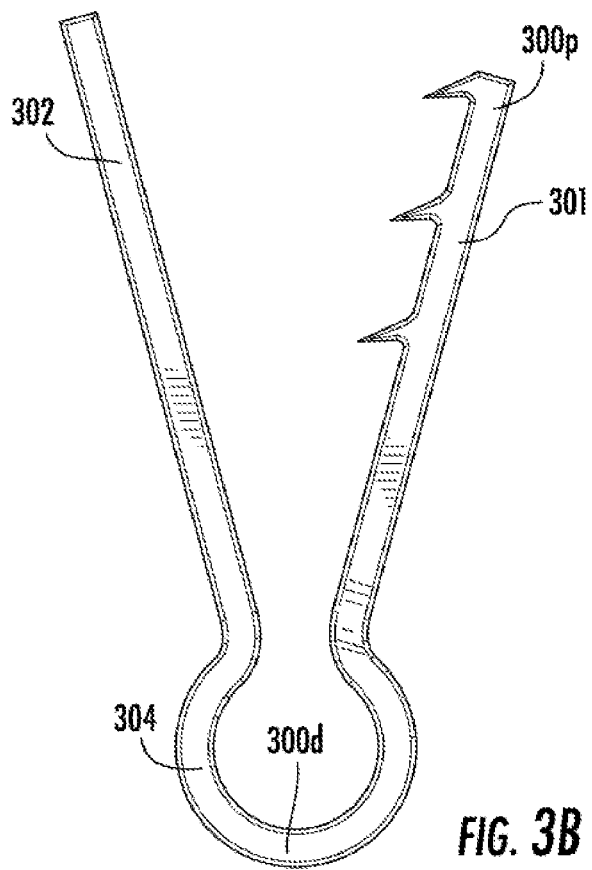
FIG. 3B illustrates a side view of the clamp in FIG. 3A.
Figure 4A:
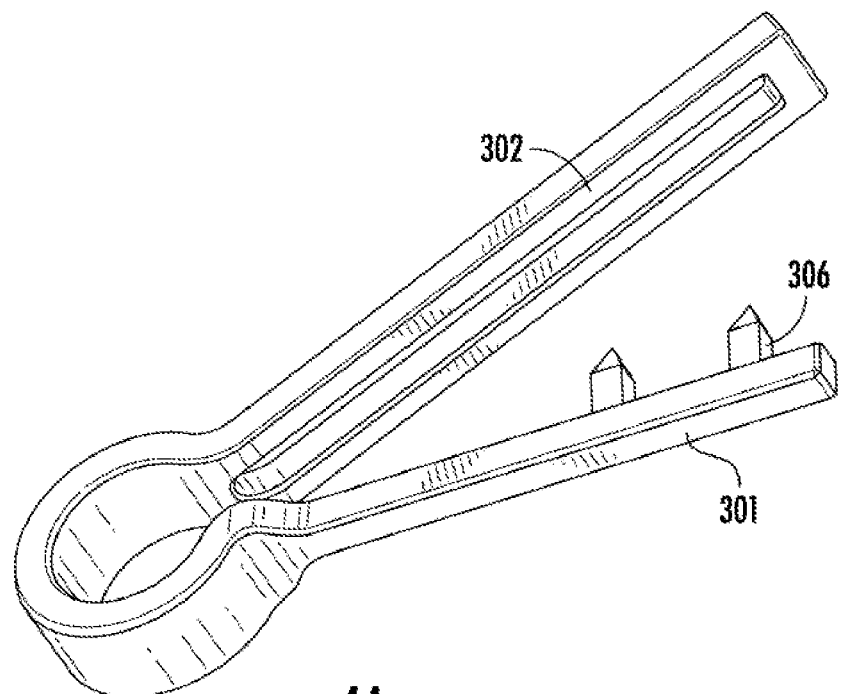
FIG. 4A illustrates a perspective view of a clamp, according to an embodiment of the present disclosure.
Figure 4B:
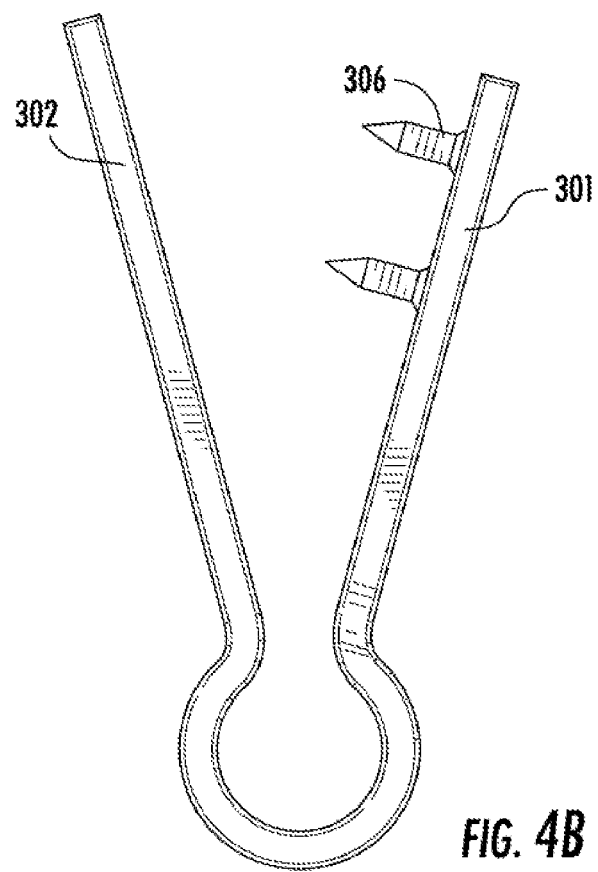
FIG. 4B illustrates a side view of the clamp in FIG. 4A.
Figure 5A:
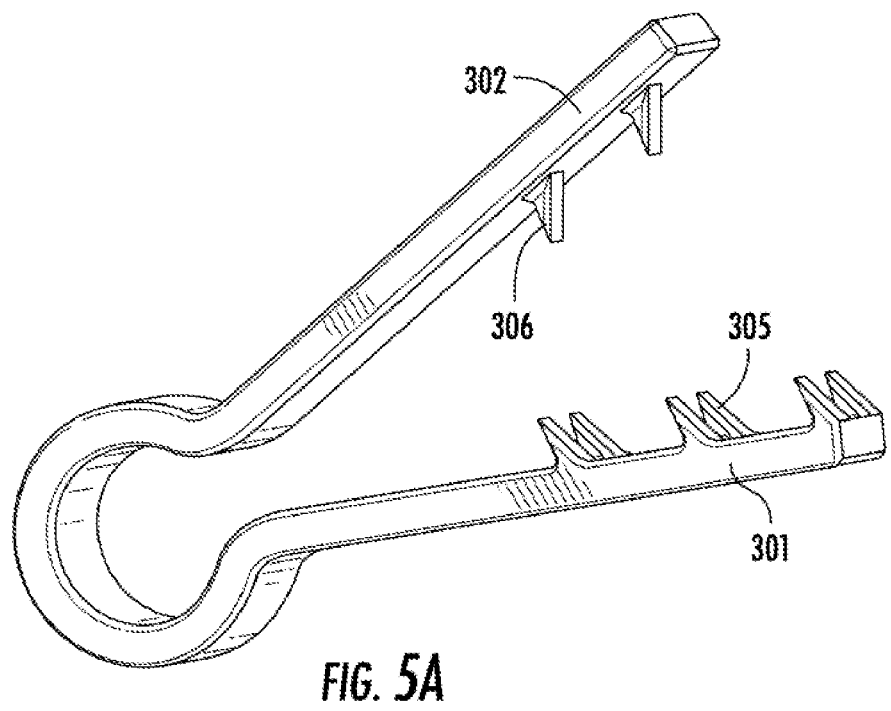
FIG. 5A illustrates a perspective view of a clamp, according to an embodiment of the present disclosure.
Figure 5B:
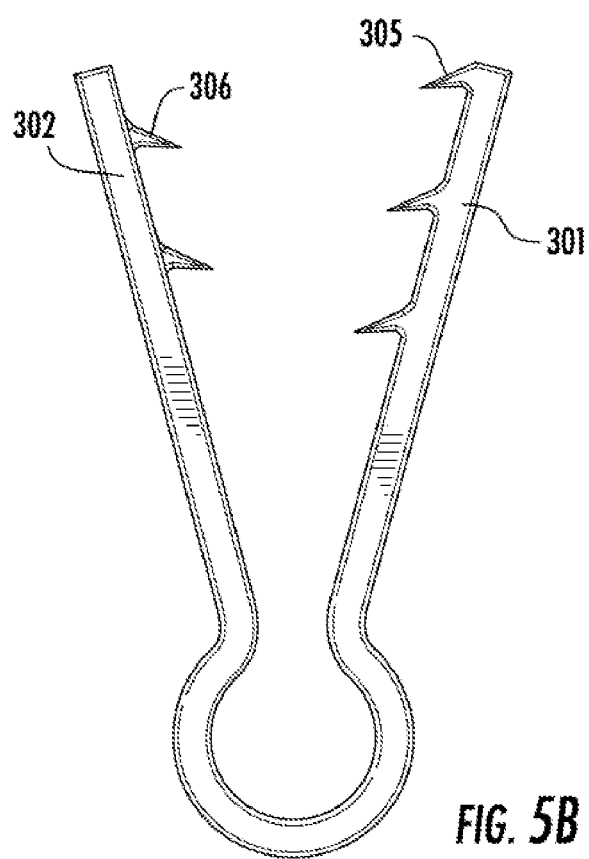
FIG. 5B illustrates a side view of the clamp in FIG. 5A.
Figure 6A:
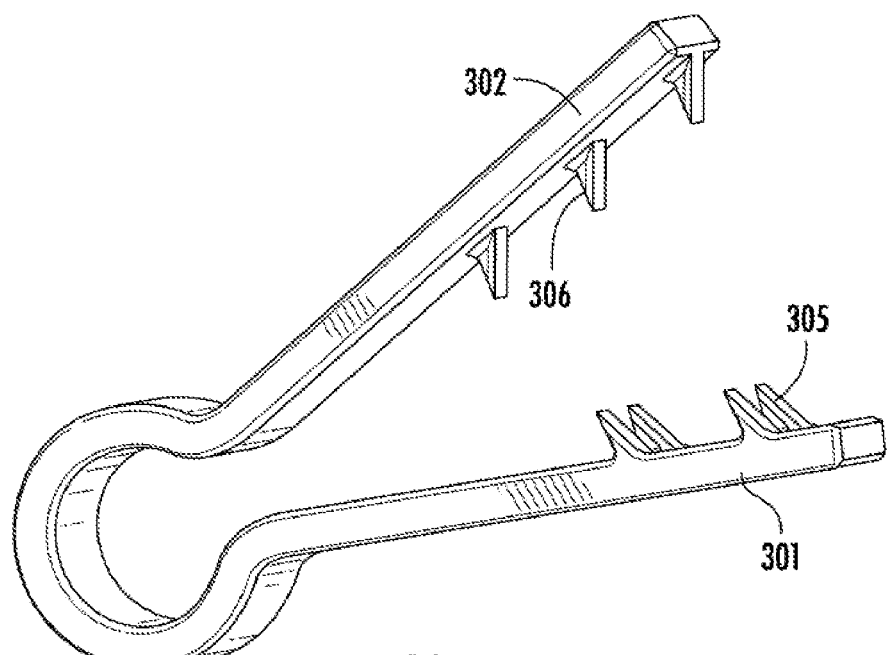
FIG. 6A illustrates a perspective view of a clamp, according to an embodiment of the present disclosure.
Figure 6B:
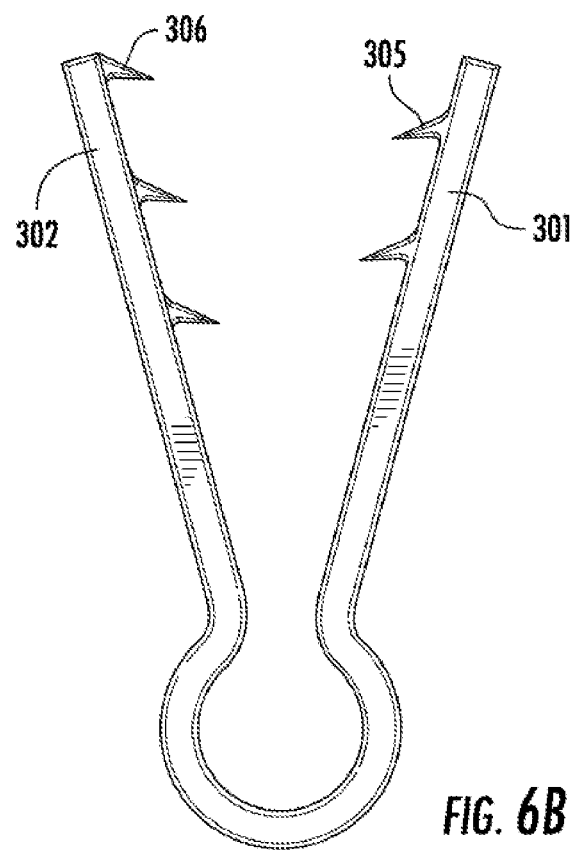
FIG. 6B illustrates a side view of the clamp in FIG. 6A.

With reference to FIGS. 3A and 3B, an embodiment of a clamp for clamping a leaflet of a heart valve according to the present disclosure is illustrated, which includes two arms 301, 302 at a first end 300p of the clamp. The arms 301, 302 can transition between a closed configuration in which the arms 301, 302 are oriented toward each other, and an open configuration in which the arms 302 are oriented away from each other at a distance between the arms 301, 302 away from each other that is greater than a distance between the arms 301, 302 in the closed configuration. A spring portion 304 at a second end 300d of the clamp is configured to bias the arms 301, 302 to the closed configuration. One arm 301 includes protrusions 306 that extend along the arm 302 that are configured to embed into tissue. Each of the protrusions 306 may be angled toward the second end 300d of the clamp 300 to resist a movement of a tissue between the arms 301, 302 with respect to the clamp by embedding the protrusions 306 into the tissue and/or providing a frictional force to the tissue. One of the arms 302 includes a slot 307 extending along a portion of the length of the arm 302 that may assist with the protrusions 306 embedding into tissue by providing a window defined by struts of the arm 302 about the protrusions 306 and/or may lighten the weight of the clamp 300 by reducing the material used compared to a clamp without a vacant slot 307. In FIGS. 4A and 4B, the protrusions 306 on an arm 301 are angled perpendicularly to the arm 301. In FIGS. 5A-6B, the protrusions 306 on one arm 302 extend along a longitudinal axis of the arm 302, while the protrusions 305 on the opposing arm 301 extend in two spaced apart columns adjacent to the longitudinal axis of the opposing arm 301. The protrusions 305 may be oriented to oppose a direction the clamp is likely to slide (e.g., oriented toward an end of a leaflet). In some embodiments, the protrusions 305 may each be in a different plane from each other to reduce tearing propagation from adjacent protrusions 305. In some embodiments, the protrusions may be barbs, spikes, hooks, tines, or the like.

In various embodiments, a clamp may be manufactured to be made up of a material adequate to provide a sufficient clamping force to fixate the clamp to a leaflet and provide a substantial anchoring body for an attached filament such as an artificial chordae tendineae. In an aspect, a clamp may be manufactured to provide sufficient force to enable the clamp to fixedly attach to the valve tissue without imparting undue gravitational forces that may disrupt efforts of valve repair. In this way, the clamp has a mass that is not significantly larger than necessary such that the weight of the clamp does not negatively impact the leaflet or nearby tissue. For example, a clamp may weigh less than about 0.10 grams, less than about 0.08 grams, or the like, e.g. such that a weight of a clamp may not undesirably interfere with leaflet operation. A clamp may comprise various materials such as, e.g., nitinol, a polymer, a rubber, nylon, stainless steel, nickel titanium, platinum, combinations thereof, or the like.

Figure 7A:
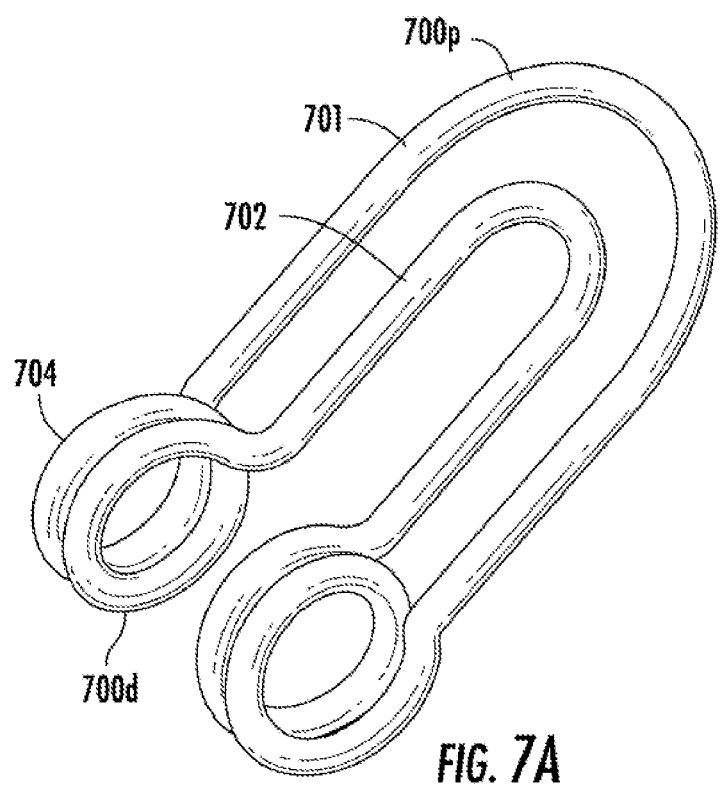
FIG. 7A illustrates a perspective view of a clamp, according to an embodiment of the present disclosure.
Figure 7B:
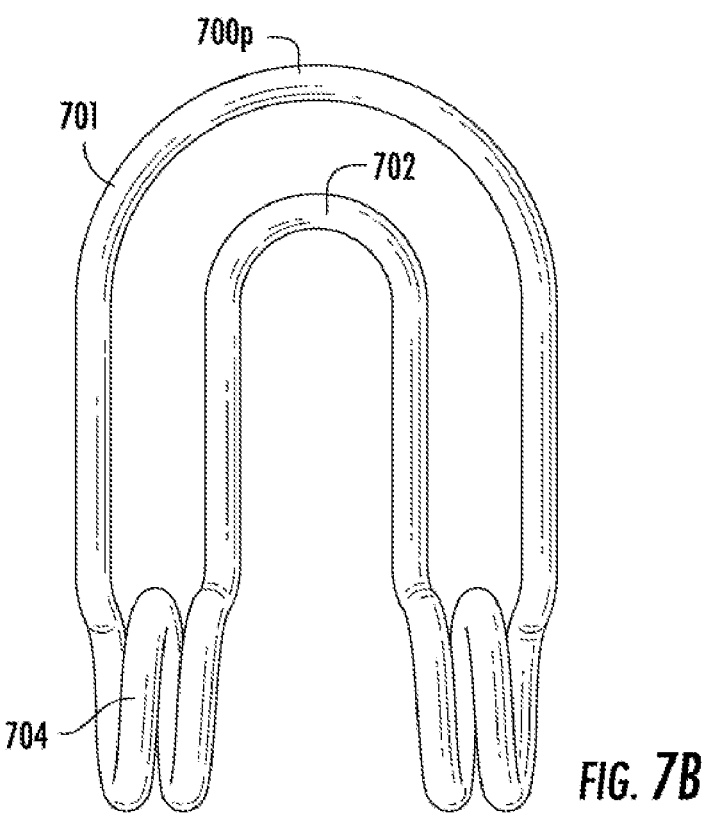
FIG. 7B illustrates a front view of the clamp in FIG. 7A.
Figure 8A:
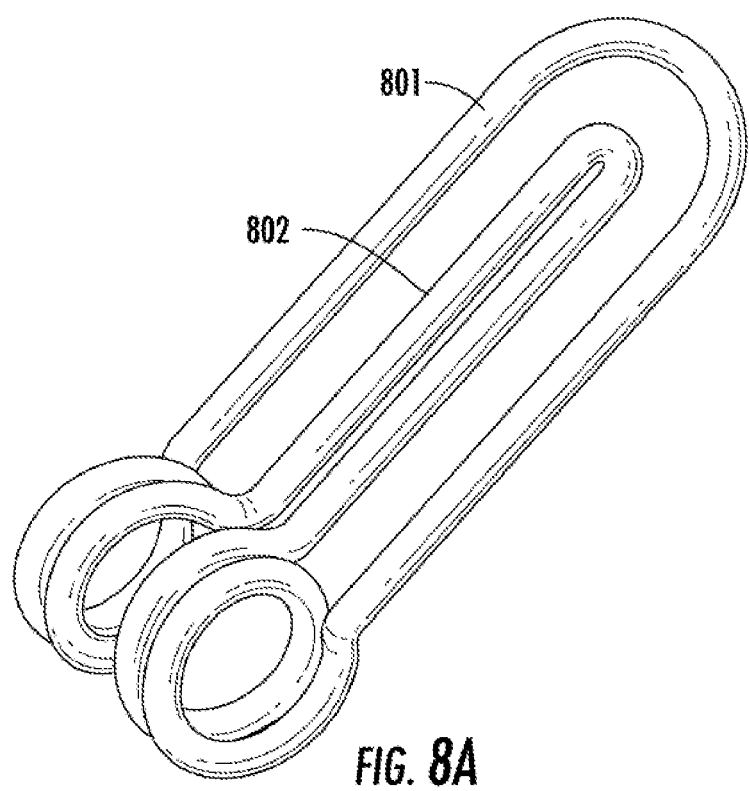
FIG. 8A illustrates a perspective view of a clamp, according to an embodiment of the present disclosure.
Figure 8B:
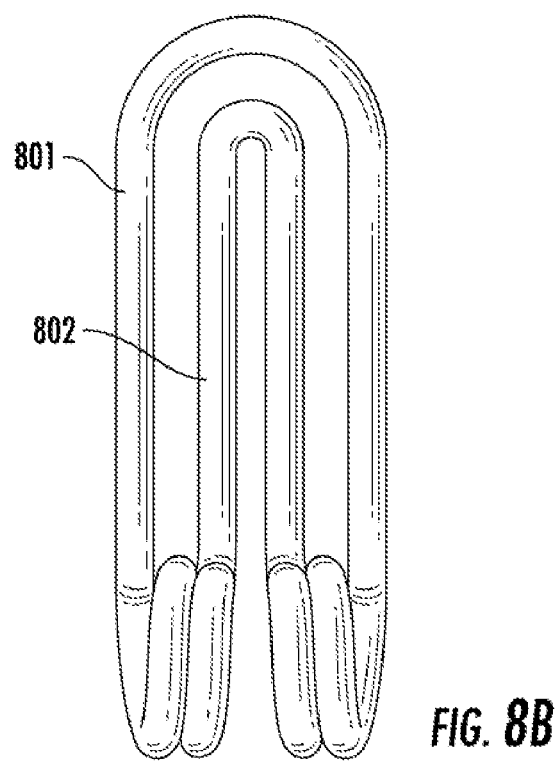
FIG. 8B illustrates a front view of the clamp in FIG. 8A.
Figure 9A:
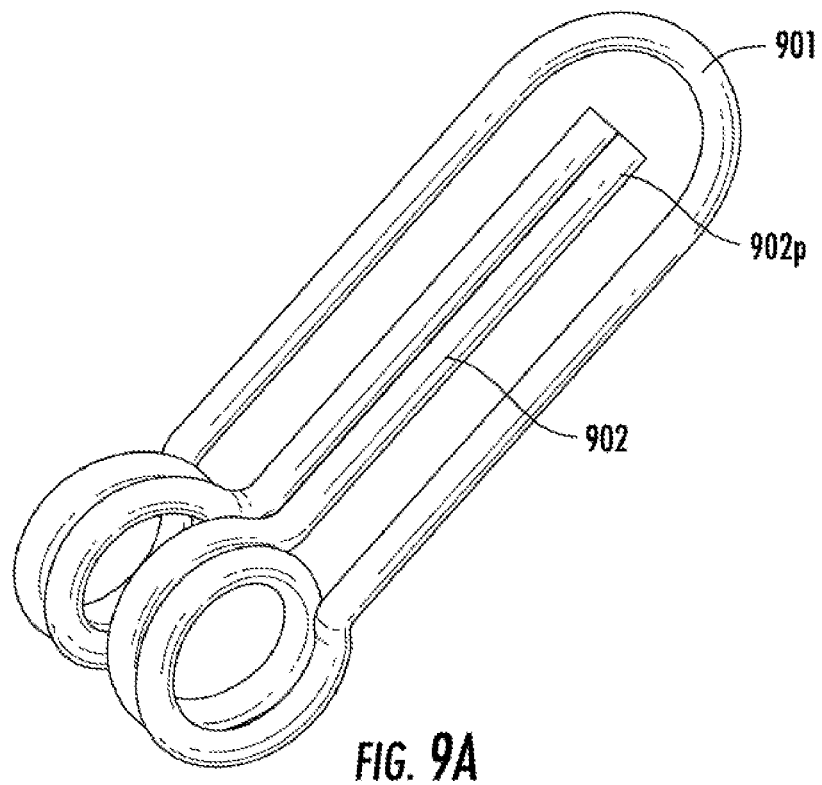
FIG. 9A illustrates a perspective view of a clamp, according to an embodiment of the present disclosure.
Figure 9B:
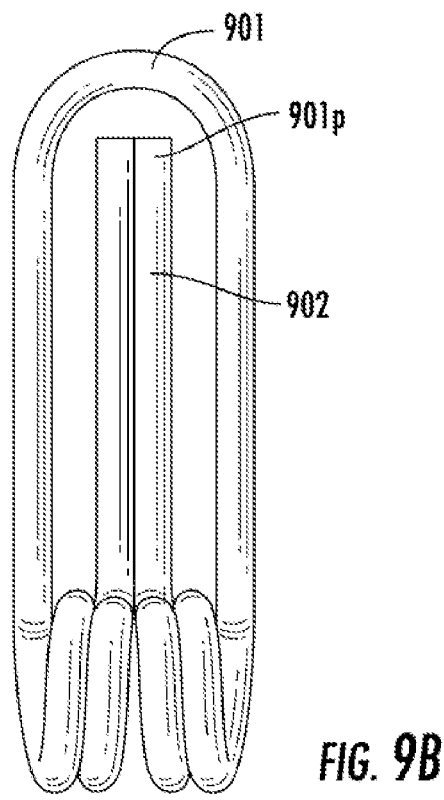
FIG. 9B illustrates a front view of the clamp in FIG. 9A.
Figure 10A:
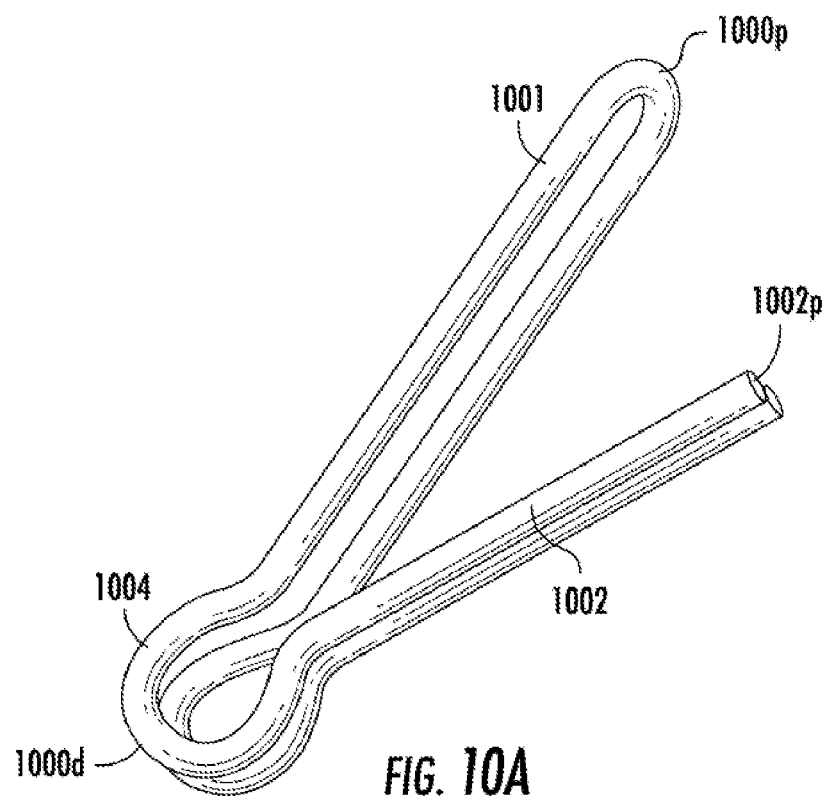
FIG. 10A illustrates a perspective view of a clamp, according to an embodiment of the present disclosure.
Figure 10B:
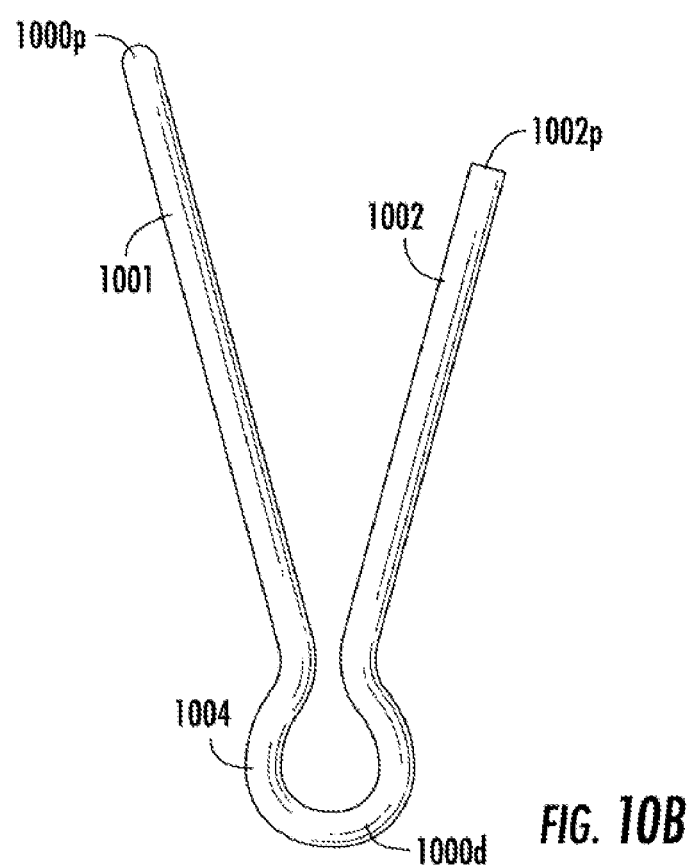
FIG. 10B illustrates a side view of the clamp in FIG. 10A.

With reference to FIGS. 7A and 7B, an embodiment of a clamp for clamping a leaflet of a heart valve according to the present disclosure is illustrated, which includes two arms 701, 702 at a first end 700p of the clamp. The arms 701, 702 can transition between a closed configuration in which the arms 701, 702 are oriented toward each other and/or are aligned substantially in the same plane, and an open configuration in which the arms 701, 702 are oriented away from each other in different relative planes. In the closed configuration, the second arm 702 extends within the first arm 701. A spring portion 704 at a second end 700d of the clamp where each of the arms 701, 702 connect to each other as part of the same wire filament making up the clamp. The spring portion 704 may be a coiled spring and is configured to bias the arms 702 to the closed configuration. A single wire filament makes up the clamp and extends from the first arm 702 to the spring portions 704 and to the second arm 702 without the wire filament terminating in an end such that there are no sharp portions of the clamp. FIGS. 8A and 8B illustrate first and second arms 801, 802 having a thinner width profile the arms 701, 702 of the clamp in FIGS. 7A and 7B. FIGS. 9A and 9B illustrate first and second arms 901, 902 with the wire filament that makes up the clamp terminating in two ends that make up an end 902p of the second arm 902. FIGS. 10A and 10B illustrate a clamp having a first arm 1001 and second arm 1002 at a first end 1000p of the clamp. The single wire filament that makes up the clamp terminates at an end 1002p of the second arm 1002. The clamp includes a spring portion 1004 at a second end 1000d of the clamp that is configured to bias the arms 1001, 1002 to the closed configuration.

Figure 11A:
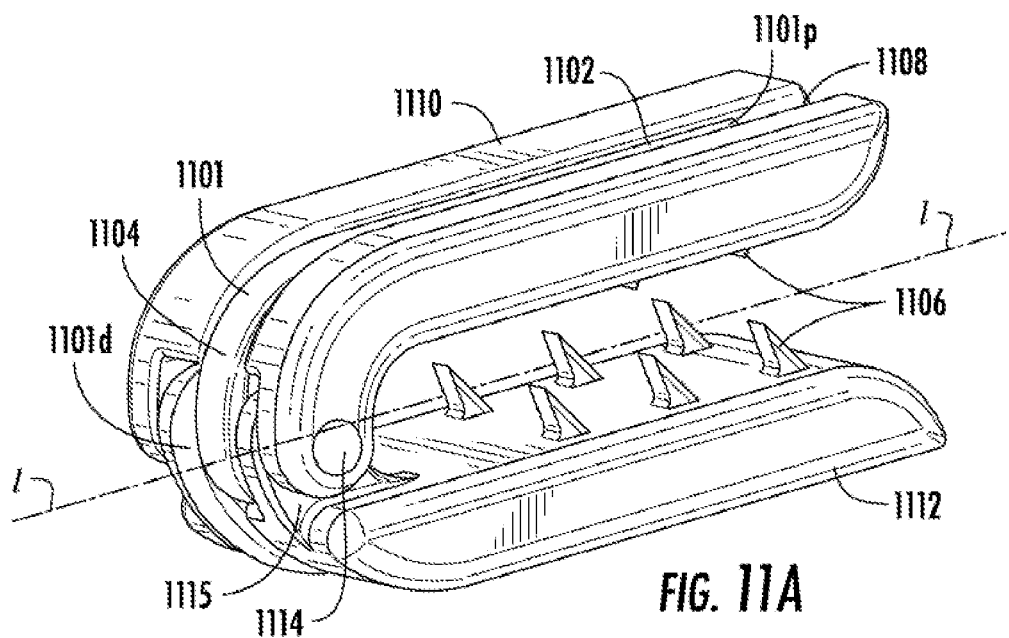
FIG. 11A illustrates a perspective view of a clamp, according to an embodiment of the present disclosure.
Figure 11B:
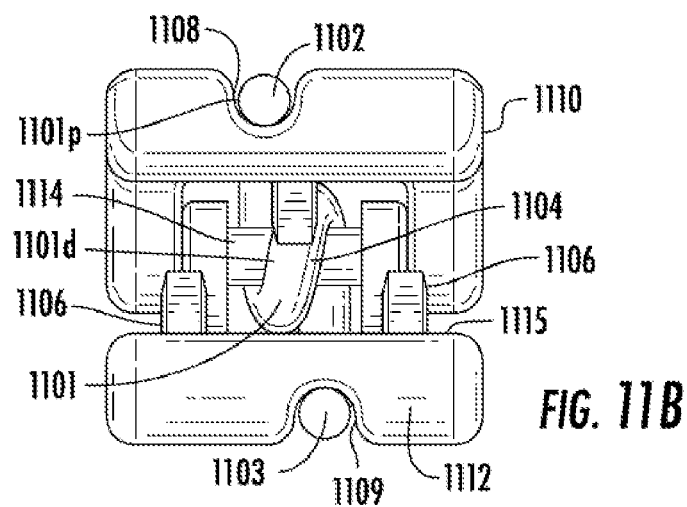
FIG. 11B illustrates a top view of the clamp of FIG. 11A.
Figure 11C:
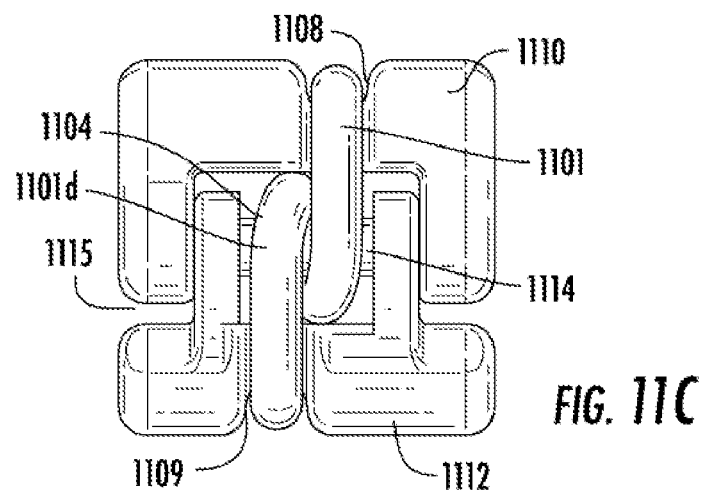
FIG. 11C illustrates a bottom view of the clamp of FIGS. 11A and 11B.

With reference to FIGS. 11A-11C, an embodiment of a clamp for clamping a leaflet of a heart valve according to the present disclosure is illustrated, which includes a body 1101 with two arms 1102, 1103 at a first end 1101p of the body 1101. The arms 1102, 1103 have a closed configuration in which the arms 1102, 1103 are oriented towards each other as illustrated in FIGS. 11A-11C, and an open configuration in which the arms 1102, 1103 are oriented away from each other. A coiled spring portion 1104 may be at a second end 1101d of the body 1101. The spring portion 1104 is configured to bias the arms 1102, 1103 to the closed configuration. A longitudinal axis € may extend through the first end 1101p and the second end 1101d. A first cover 1110 may be disposed adjacent to an arm 1102 and may extend along the arm 1102 to the longitudinal axis €. A second cover 1112 may be disposed adjacent to the opposing arm 1102 and may extend along the arm 1102 to the longitudinal axis €. The covers 1110, 1112 include protrusions 1106 that extend along the covers 1110, 1112 and that are configured to embed into tissue. A pin 1114 may extend through the first cover 1110, the second cover 1112, the coiled spring portion 1104, and the longitudinal axis €. A first channel 1108 may be disposed on the first cover 1110 extending along the first cover 1100 and has a central axis that may be substantially parallel with an arm 1102. A second channel 1109 may be disposed on the second cover 1112 extending along the second cover 1112 and has a central axis that may be substantially parallel with the opposing arm 1103. The channels 1108, 1109 accommodate the arms 1102, 1103, and each channel 1108, 1109 has a portion without an arm 1102, 1103 extending away from each of the arms 1102, 1103 that can accommodate a pin (e.g., a locking pin of a spreader as described below). The covers 1110, 1112 are rotatable about the pin 1114 to move with the opening and closing of the arms 1102, 1103. The covers include a clearance space 1115 near the pin 1114 to allow for this rotation without the covers 1110, 1112 interfering with each other.

Figure 12A:
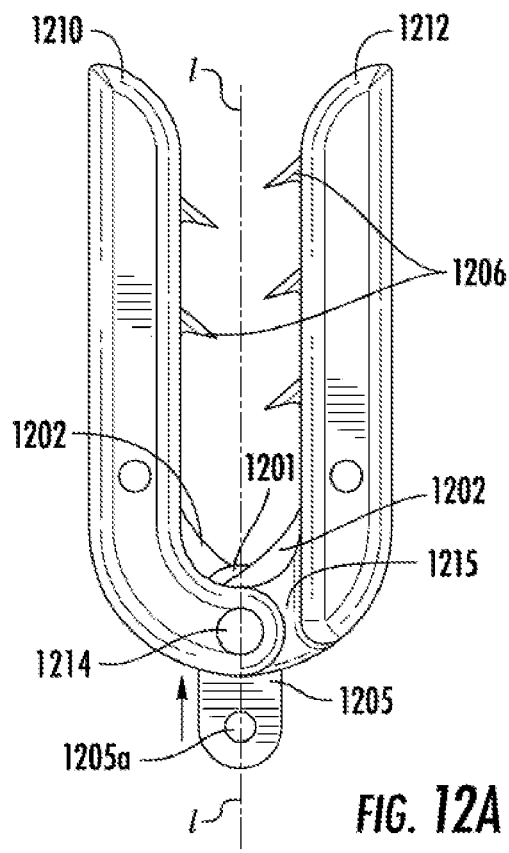
FIG. 12A illustrates a side view of a clamp in a closed configuration, according to an embodiment of the present disclosure.
Figure 12B:
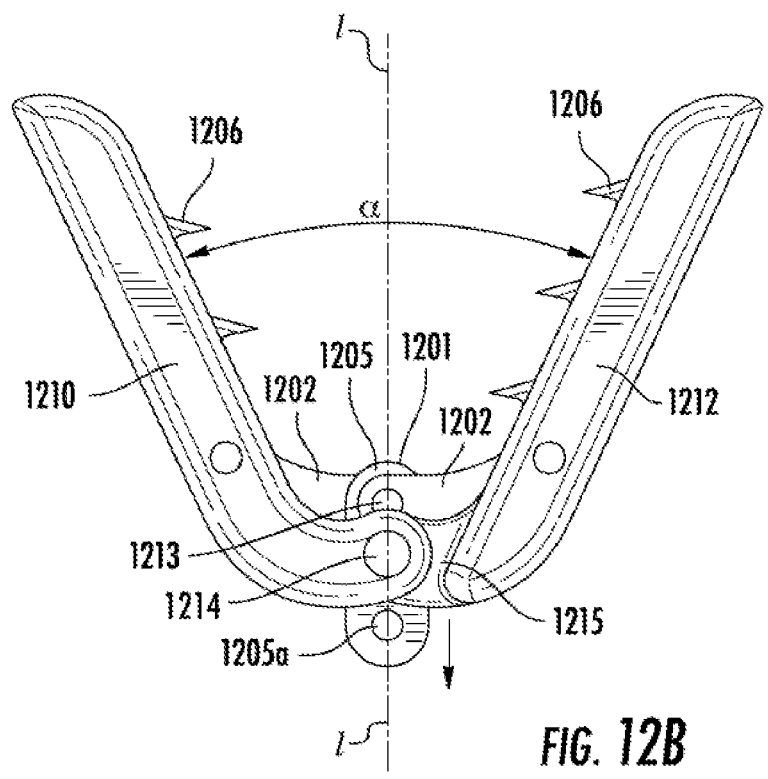
FIG. 12B illustrates the clamp of FIG. 12A in an open configuration.

With reference to FIGS. 12A and 12B, an embodiment of a clamp for clamping a leaflet of a heart valve according to the present disclosure is illustrated, which includes a frame body 1201 with two arms 1202 pivotably connected via a tab 1205. A first pin 1213 extends through the two arms 1202 and the tab 1205 of the frame body 1201 such that the arms 1202 may rotate about the first pin 1213. A first cover 1210 may be disposed adjacent to an arm 1202 and may extend along the arm 1202 to a longitudinal axis €. A second cover 1212 may be disposed adjacent to the opposing arm 1202 and may extend along the arm 1202 to the longitudinal axis €. The covers 1210, 1212 include protrusions 1206 that extend along the covers 1210, 1212 and that are configured to embed into tissue. A second pin 1214 may extend through the first cover 1210, the second cover 1212, and the longitudinal axis €. The arms 1202 have a stable closed configuration, as illustrated in FIG. 12A, in which the arms 1202 are configured for engagement to a tissue, and a stable open configuration, as illustrated in FIG. 12B, in which the arms 1202 are spaced apart from each other. The open configuration may separate the arms 1202 by a given number of degrees apart from each other a, e.g., about 50°, about 60°, about 90°, etc. The clamp transitions between the closed and open configurations by translating the tab 1205 along the longitudinal axis € such that the arms 1202 of the frame body 1201 move apart and toward each other along with the covers 1210, 1212. As the tab 1205 is moved along the longitudinal axis €, the arms 1202 rotate about the first pin 1213 and the covers 1210, 1212 rotate about the second pin 1214. The tab 1205 may be manipulated through a tab aperture 1205a (e.g., via a filament, a wire, a tether, a push member, a catheter, a bowden cable, or the like). The tab 1205 may travel a distance to transition the arms 1202 between the open and closed configurations that may be, e.g., about 0.02 inches (about 0.51 millimeters), or the like. The covers 1210, 1212 include a clearance space 1215 adjacent the pin 1214 to allow for rotation without the covers 1210, 1212 interfering with each other.

Figure 13A:
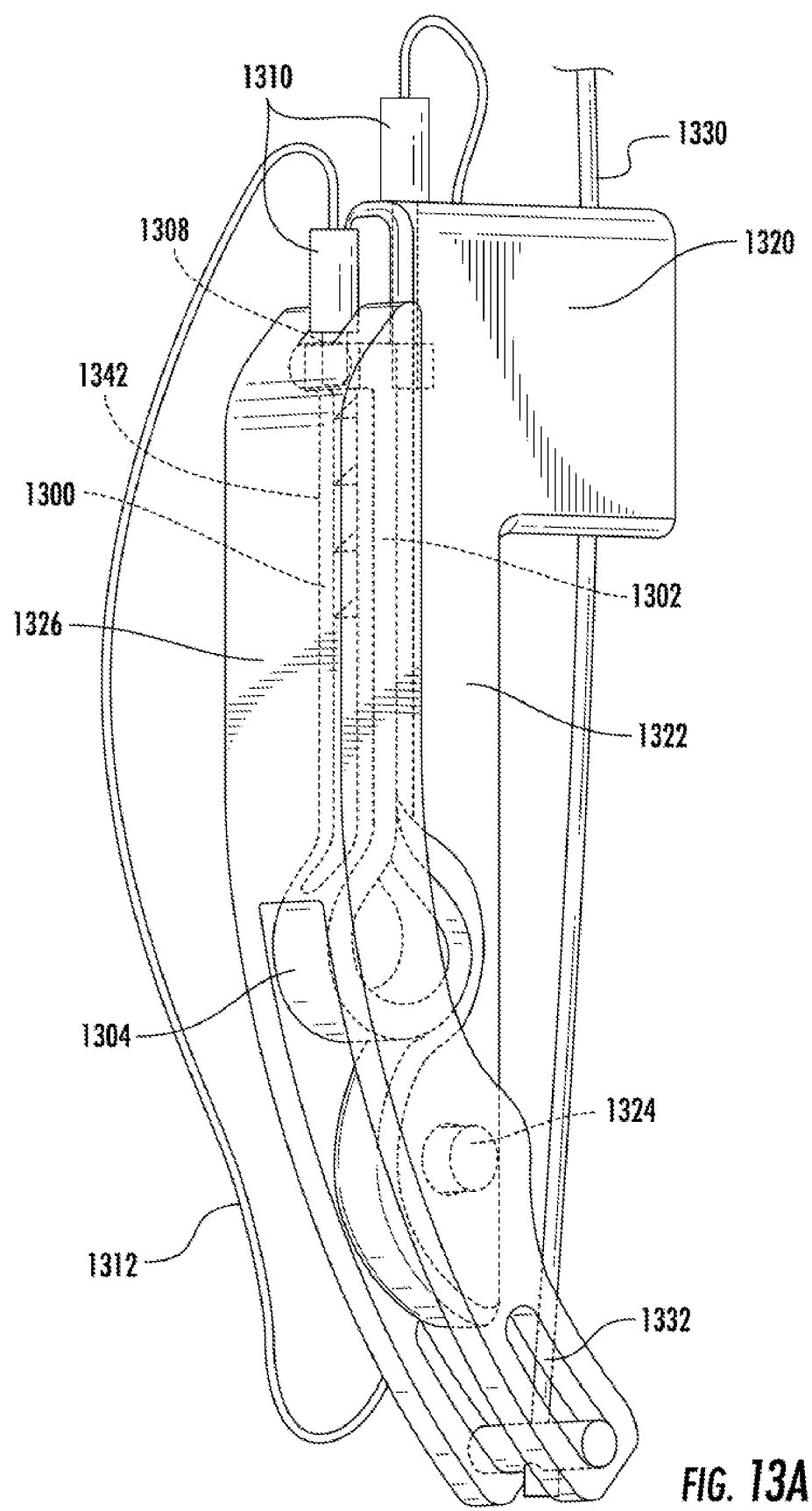
FIG. 13A illustrates a perspective view of a system for clamping a leaflet of a heart valve in a closed configuration, according to an embodiment of the present disclosure.
Figure 13B:
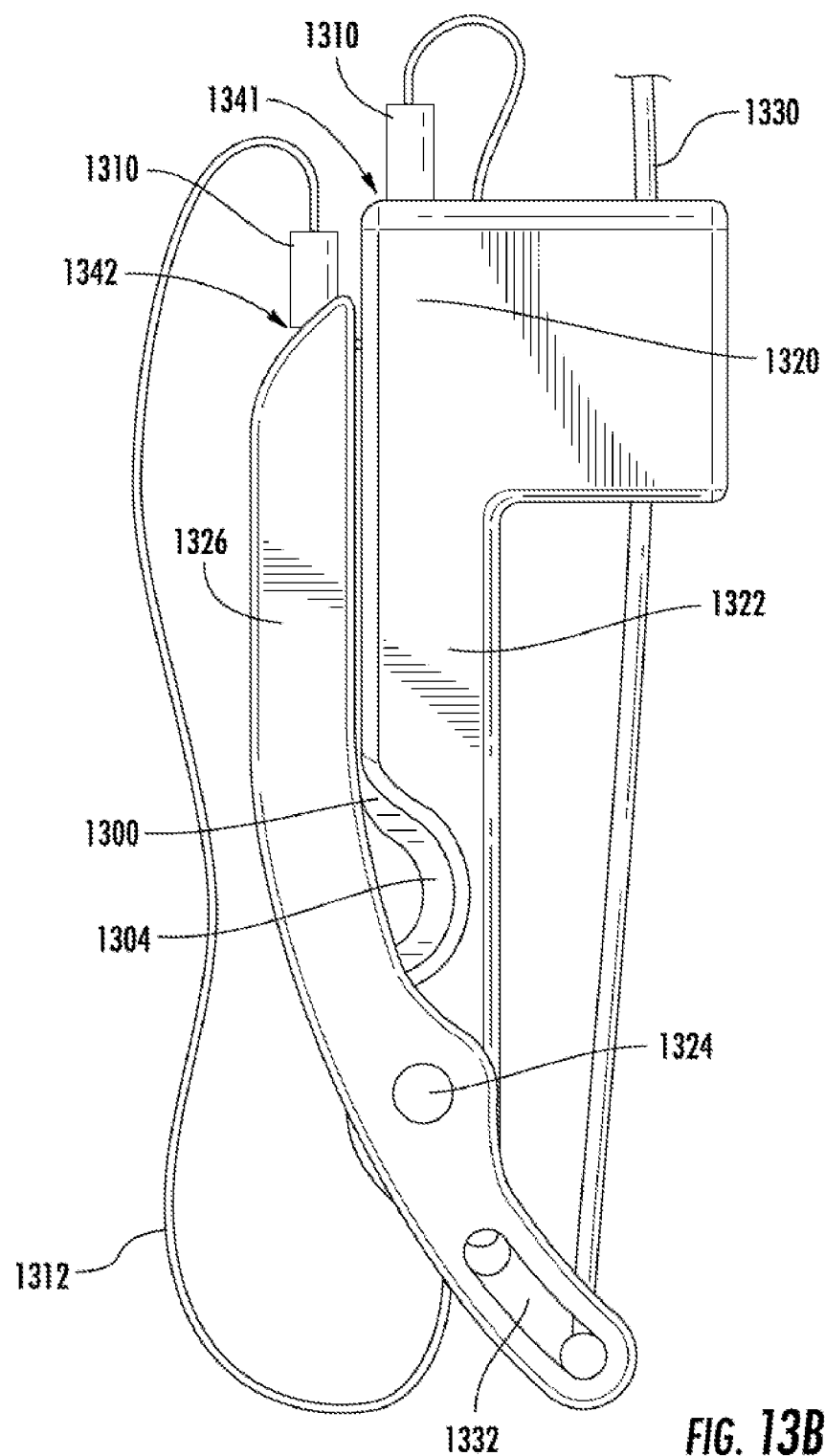
FIG. 13B illustrates a side view of the system of FIG. 13A.
Figure 13C:
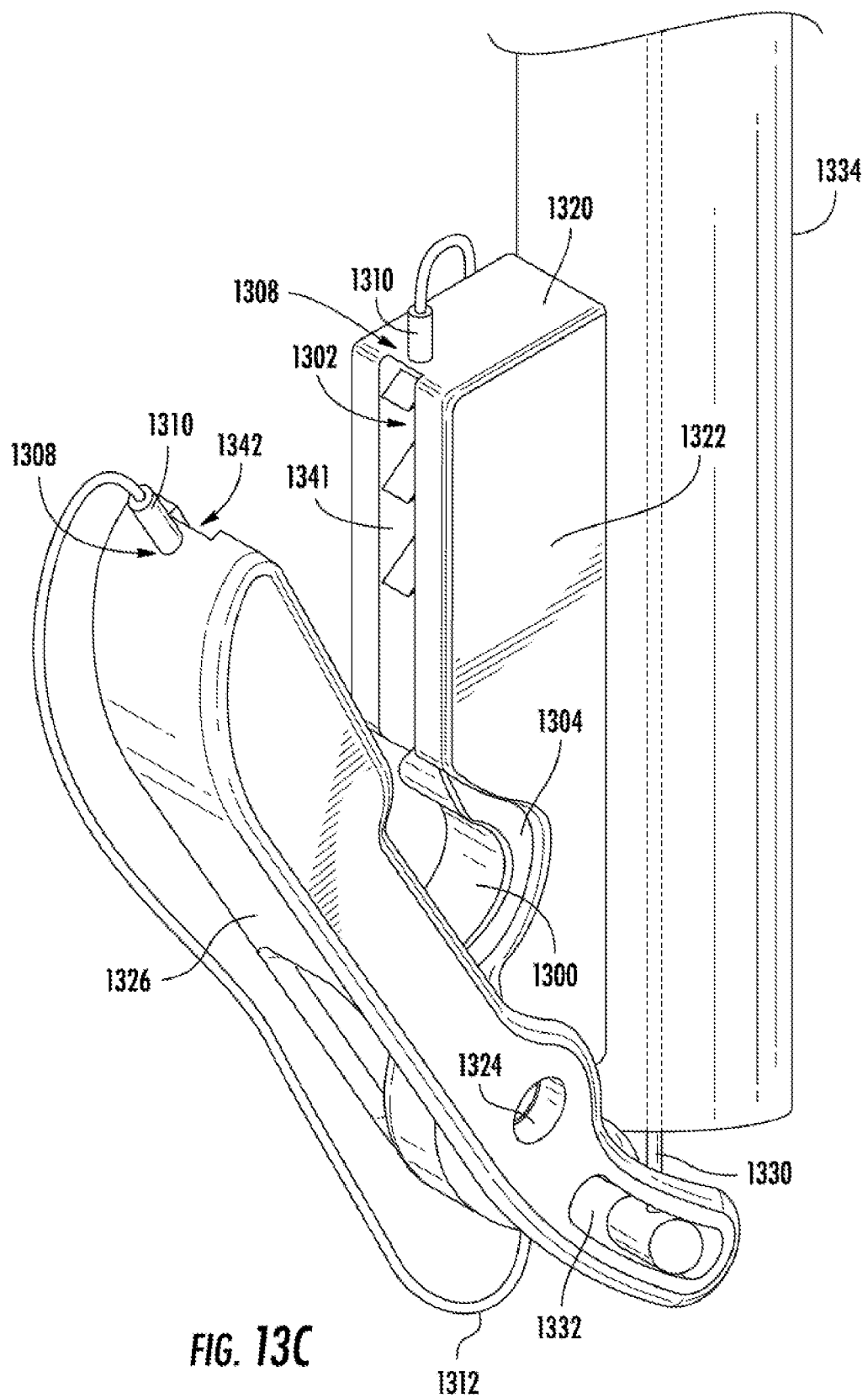
FIG. 13C illustrates the system of FIGS. 13A and 13B disposed on a catheter in an open configuration.

With reference to FIGS. 13A-13C, an embodiment system for clamping a leaflet of a heart valve according to the present disclosure is illustrated, including a clamp 1300 with arms 1302 at a first end that have a closed configuration and an open configuration, as described throughout this disclosure. The clamp 1300 is in the closed configuration in FIGS. 13A and 13B, and the clamp 1300 is in the open configuration in FIG. 13C. The clamp 1300 has a spring portion 1304 at a second end that biases the arms 1302 to the closed configuration. A spreader 1320 may be releasably coupled to the clamp 1300. The spreader 1320 may transition the clamp 1300 between the closed configuration and the open configuration. The spreader 1320 includes a base 1322 with a first pin 1324 extending from the base 1322. A lever 1326 may be rotatably disposed about the first pin 1324. The base 1322 includes a first channel 1341, and the lever 1326 includes a second channel 1342, each channel configured to accept an arm 1302 of the clamp 1300. The ends of each arm 1302 include an aperture 1308. Each aperture 1308 has a central axis that extends substantially along each of the arms 1302 and is configured to accept one of two locking pins 1310. One locking pin 1310 extends through the first channel 1341 and into the aperture 1308 of an arm 1302, while the other locking pin 1310 extends through the second channel 1342 and into the aperture 1308 of the opposing arm 1302. The locking pins 1310 fix the arms 1302 to the base 1322 and the lever 1326 such that the spreader 1320 can manipulate the arms 1302 between the open and closed configurations and so that the clamp 1300 cannot be released from the spreader 1320. Because the arms 1302 are locked within the channels 1341, 1342, the arms 1302 may transition between the closed configuration and the open configuration with a movement of the lever 1326. The lever 1326 may move about the first pin 1324 via translation of a first filament 1330 that may be coupled to a slot 1332 of the lever 1326. As the lever 1326 rotates about the first pin 1324, it also moves the arm 1302 that is within the second channel 1342 while the opposing arm 1302 is fixed within the first channel 1341 of the base 1322. In some embodiments, the pins 1310 may extend through a third and a fourth aperture in each of the base 1322 and the lever 1326 rather than the first and second channels 1341, 1342, while still extending into the apertures 1308. A second filament 1312 may be coupled at each end to the locking pins 1310 such that the second filament 1312 may be grasped and pulled such that the locking pins 1310 are removed from the apertures 1308 and channels 1341, 1342, thereby releasing the arms 1302 from the base 1322 and the lever 1326. FIG. 13C illustrates the base 1322 of the spreader 1320 coupled to a distal end of a catheter 1334. The first filament 1330 extends proximally into the catheter 1334 to be manipulated by a medical professional. Because the base 1320 is coupled to the catheter 1334, the catheter 1334 may be inserted into a patient to a target location to deliver the clamp 1300. Also, because the base 1322 is fixed to the catheter 1334, as the first filament 1330 manipulates the lever 1326 containing an arm 1302, the lever 1326 works against the bias of the spring portion 1304 and moves the clamp 1300 from the closed configuration to the open configuration by moving the arm 1302 in the lever 1326 away from the fixed arm 1302 in the base 1322.

Still referring to FIGS. 13A-13C, an embodiment of a method of clamping a leaflet of a heart valve according to the present disclosure may include inserting the catheter 1334 toward a valve (e.g., through the valve). In some embodiments, the catheter 1334 may include the spreader 1320 disposed on a distal end of the catheter 1334, which may be reversibly coupled to the clamp 1300 in a closed configuration for navigating through the patient and/or a working channel. Once the catheter 1334 is near the target site of the valve, the clamp 1300 may be transitioned to the open configuration by pulling proximally on the first filament 1330 coupled to the lever 1326 and holding tension on the first filament 1330. The lever 1326 rotates about the first pin 1324 and moves an arm 1302 within the lever 1326 apart from the opposing arm 1302 in the base 1322. With the clamp 1300 in the open configuration, the catheter 1334 may move the clamp into position proximate a leaflet (e.g., about a flailing leaflet) of the valve such that an arm 1302 is on either side of the leaflet (e.g., see FIGS. 14A-15 as discussed below). With the clamp 1300 in position about the leaflet, tension may be released on the first filament 1330, allowing the biased spring portion 1304 of the clamp 1300 to transition the clamp 1300 into the closed configuration about the leaflet. The medical professional may optionally re-open the spreader 1320 and clamp 1300 by again pulling proximally on the first filament 1330 to reposition the clamp 1300 if desired. Repositioning the clamp 1300 may be desirable, e.g., if accidently released, if a better position is realized after deploying the clamp 1300, or to configure a tension in an artificial chordae tendineae attached to the clamp 1300.

Once the clamp 1300 is in position, the second filament 1312 attached to the locking pins 1310 may be pulled (e.g., by a grasper, a third filament, or the like) such that the pins 1310 are removed from the apertures 1308 of the arms 1302. With the pins 1310 removed, the clamp is no longer fixed to the spreader 1320 and the spreader 1320 releases the clamp 1300. The clamp 1300 may be left delivered on the leaflet, and the catheter 1334 and spreader 1320 may be withdrawn from the patient in an open configuration (e.g., within an outer sheath) or a closed configuration (e.g., by a spring within the spreader 1320 to bias the lever 1326 toward the base 1322). Additionally, or in the alternative, a clamp may be delivered with a fourth filament (e.g., artificial chordae tendineae) that may extend from the clamp 1300 (e.g., from the spring portion 1304) to another device (e.g., an anchor) to be used in a medical treatment (e.g., anchoring artificial chordae tendineae to a leaflet and to a papillary muscle).

Figure 14A:
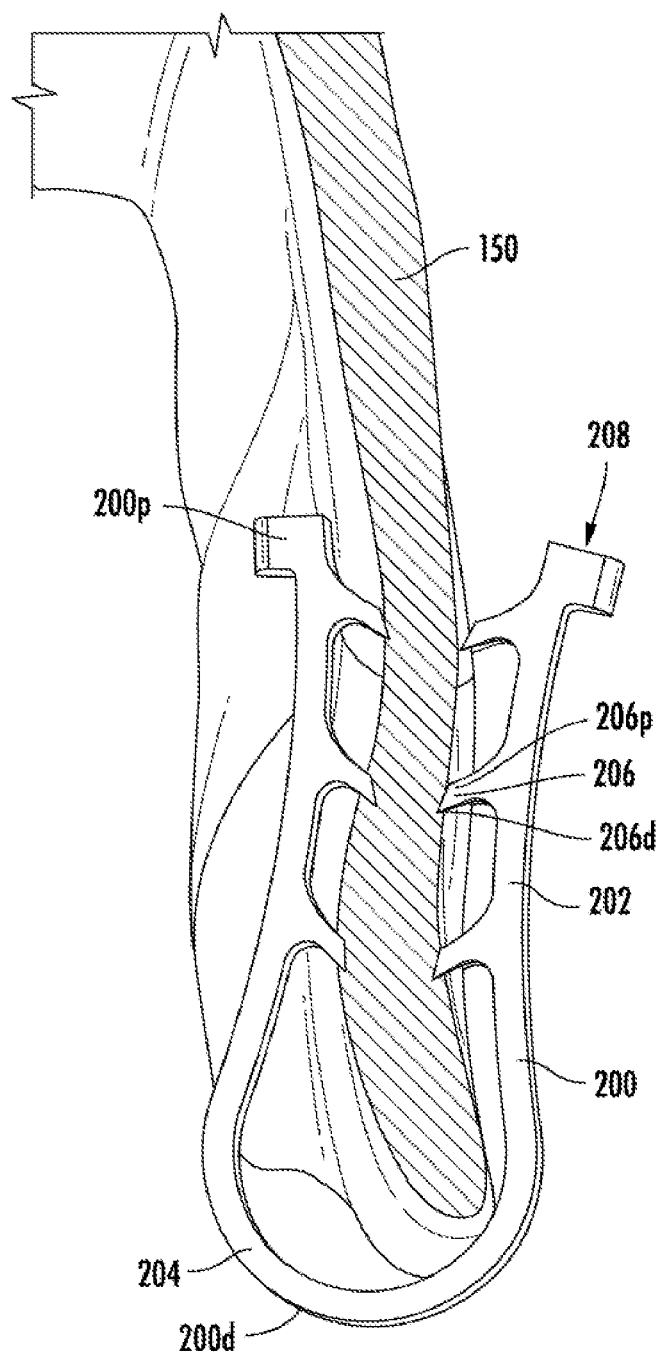
FIG. 14A illustrates a cross-sectional view of a clamp clamping a leaflet of a heart valve, according to an embodiment of the present disclosure.
Figure 14C:
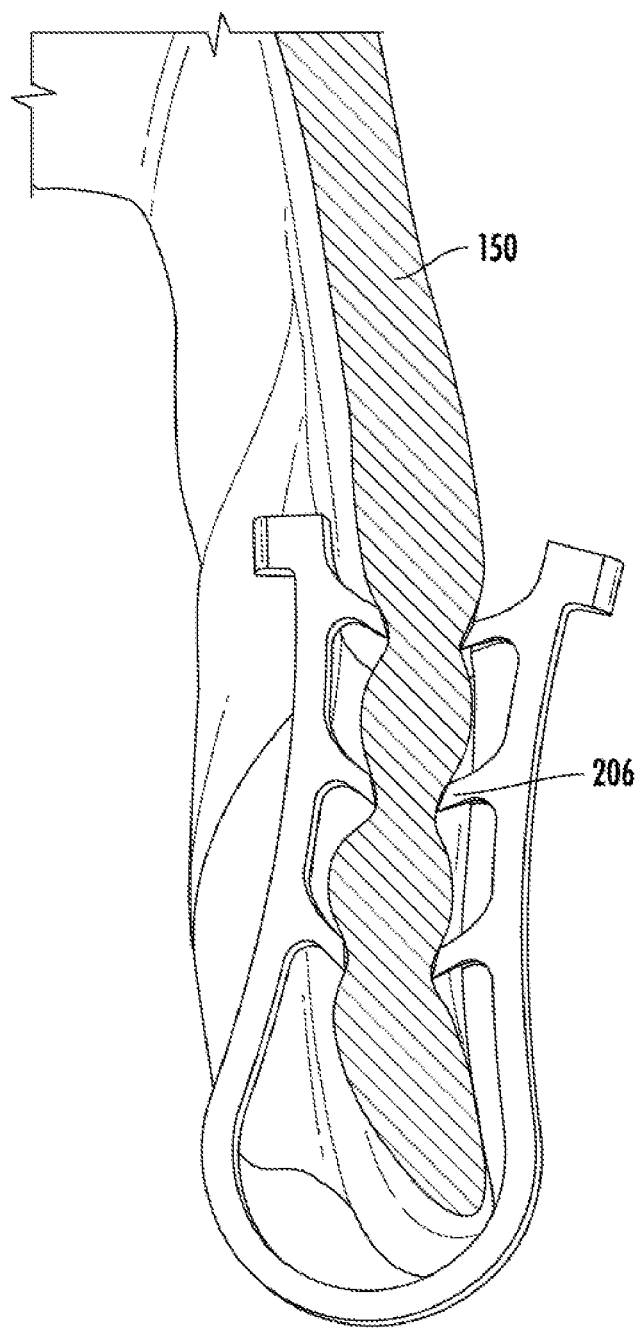
FIG. 14C illustrates another cross-sectional view of an alternative orientation of the clamp and leaflet of FIG. 14A.

With reference to FIGS. 14A and 14B, the embodiment of a clamp 200 of FIGS. 2A-2E is illustrated clamping a leaflet 150 of a heart valve according to the present disclosure. The clamp 200 is shown in the closed configuration with its two arms 202 adjacent the leaflet 150, with one arm 202 on either side of the leaflet 150. The spring portion 204 at the second end 200d of the clamp 200 is biasing the two arms 202 toward each other in this closed configuration. In the illustrated embodiment, the clamp 200 has been disposed about the leaflet by leading with the first end 200p and with the leaflet 150 entering between the two arms 202. The clamp 200 may have been delivered onto the leaflet 150 using another device, e.g., a spreader, that can articulate the arms 202 between the open configuration for accepting the leaflet 150 and the closed configuration for engaging the leaflet 150. The clamp 200 may have been unlocked from the spreader for delivery by, e.g., removing locking pins from the apertures 208. As the clamp 200 was delivered onto the leaflet 150, the leaflet 150 may have engaged one or more smooth surfaces 206p of the protrusions 206. In the closed configuration, the engaging ends 206d of most of the protrusions may be at least partially embedded into the leaflet 150. The embedded protrusions 206 enter less than about 50% of a thickness of a wall of the leaflet 150. The spring portion 204 is configured to provide a clamping force that compresses the arms 202 and/or protrusions 206 onto the leaflet 150 and may embed the protrusions 206. In some embodiments, protrusions and/or a spring portion may be configured to embed less than about 25% of a wall of a leaflet, less than 10% of a wall of a leaflet, more than 50% of a wall of a leaflet, or the like, e.g., with reference to FIG. 14C, the protrusions 206 may not extend into the wall of the leaflet 150 and may instead distort the leaflet between the protrusions 206 such that the clamp is engaged with the leaflet 150 without the protrusions 206 extending into the leaflet. A shape of the clamp, e.g., the spring portion 204 and/or the arms 202 of the clamp, may provide an amount of force that does not pierce the protrusions 206 into and/or through the leaflet 150 leaving room for the leaflet 150 to be distorted within the clamp. In some embodiments, the protrusions may extend a distance from an arm that may be about 0.1 millimeters to about 2.0 millimeters, about 0.5 millimeters to about 1.5 millimeters, about 0.7 millimeters, or the like. In some embodiments, protrusions and/or spring portions may be configured such that a tissue is not punctured by the protrusions so that the clamp may be repositioned from a first delivery site to a second delivery site without significant impact on the first delivery site. In this delivered position, the arms 202 of the clamp 200 are fixedly engaged with the leaflet 150 and the second end 200d of the clamp 200 may be coupled to a filament, e.g., one or more artificial chordae tendineae, such as described and illustrated with respect to FIG. 15.

With reference to FIG. 15, an embodiment of a system for clamping a leaflet 150 of a heart valve according to the present disclosure is illustrated, including four clamps 1500 attached to the leaflet 150. Each of the clamps 1500 is attached to an end of a filament 1550 that is an artificial chordae tendineae. The filaments 1550 are attached to an anchoring filament 1552 that is further attached to an anchor 1554. The anchor 1554 is embedded in papillary muscle 152 of the heart 154. A medical professional may adjust the length and tension of the filaments 1550 and anchoring filaments 1552 such that they may replicate and/or replace chordae tendineae of the heart 154 for function with the leaflet 150 of the valve by varying the length of the filaments 1550, 1552 between the clamp(s) 1500 and the anchor 1554. The medical professional may adjust filaments 1550, 1552 in response to a heart valve regurgitation observation that may be observed via transesophageal echocardiogram and/or fluoroscopy. The filaments 1550, 1552 are fixed at one end to the leaflet 150 by the clamp(s) 1500 and are fixed at a second end to the papillary muscle 152 by the anchor(s) 1554. A single anchoring filament 1552 may be coupled to one or more filaments 1550 such that one anchoring filament 1552 and one anchor 1554 may be used for multiple clamps 1500. In some embodiments, the filaments 1552 and anchoring filaments 1552 may be coupled to one or more clamps 1500 and to each other during delivery of the system into the heart 154.

Figure 16:
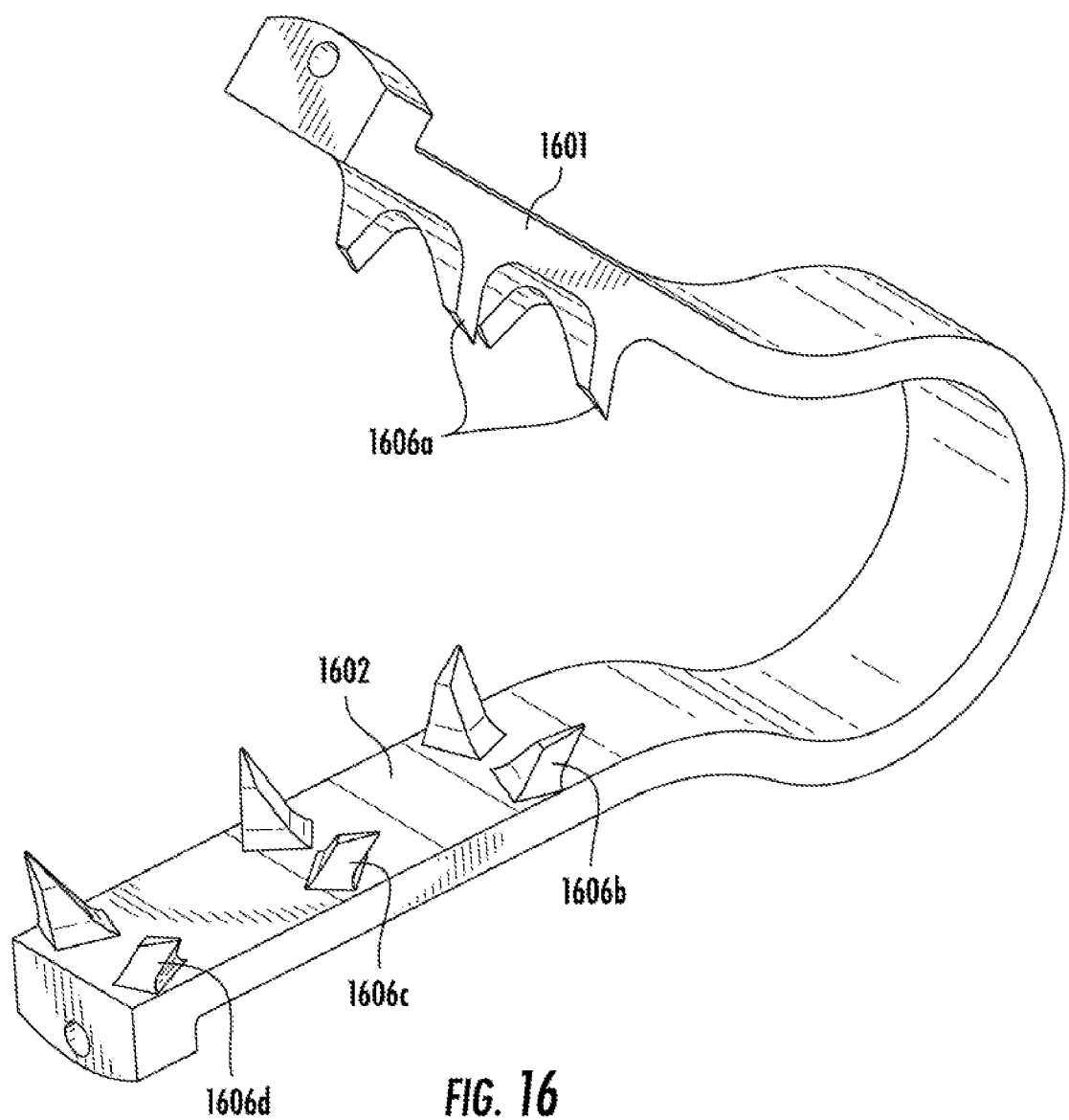
FIG. 16 illustrates a perspective view of the clamp in FIGS. 2A-2E having alternative protrusions, according to an embodiment of the present disclosure.

FIG. 16 illustrates a perspective view of the clamp in FIGS. 2A-2D having alternative protrusions 1606a, 1606b, 1606c, and 1606d, according to an embodiment of the present disclosure. The clamp includes protrusions 1606a, 1606b, 1606c, and 1606d oriented at various angles that are offset from each other and/or the arms 1601, 1602. The first protrusions 1606a are oriented at a first angle with respect to a longitudinal axis of the first arm 1601. The second protrusions 1606b are oriented at a second angle with respect to a longitudinal axis of the second arm 1602 that is larger than the first angle. The third protrusions 1606c are oriented at a third angle with respect to the longitudinal axis of the second arm 1602 that is larger than the second angle. The fourth protrusions 1606d are oriented at a fourth angle with respect to the longitudinal axis of the second arm 1602 that is larger than the third angle. Various embodiments may include multiple protrusions at various angles. Some protrusions may engage tissue at alternative angles from other protrusions along the same arm or an opposing arm of a clamp.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:
1. A system for clamping a leaflet of a heart valve, the system comprising:
    a clamp comprising:

a plurality of arms at a first end, the plurality of arms having a closed configuration in which the arms are oriented toward each other, and an open configuration in which the arms are oriented away from each other at an open distance between the arms that is greater than a closed distance between the arms in the closed configuration; and a spring portion coupled to the plurality of arms at a second end, the spring portion configured to bias the arms to the closed configuration;

wherein the arms of the clamp are configured to fixedly engage with a leaflet of the heart valve and the second end of the clamp is configured to couple to an artificial chordae tendineae;

a spreader configured to transition the clamp between the closed configuration and the open configuration, the spreader comprising:

a base;

a lever rotatable with respect to the base;

a first channel extending through the base and configured to accept one of the plurality of arms; and a second channel extending through the lever and configured to accept one of the plurality of arms; and a first filament extending from the lever, the first filament configured to move the lever and the clamp between the closed configuration and the open configuration of the clamp.

2. The system of claim 1, wherein a first aperture is defined in one of the plurality of arms of the clamp and the first channel extending through the base is substantially parallel with the first aperture; and a second aperture is defined in another of the plurality of arms of the clamp and the second channel extending through the lever is substantially parallel with the second aperture.

3. The system of claim 2, further comprising a first pin disposed within the first aperture and the first channel, and a second pin disposed within the second aperture and the second channel.

4. The system of claim 3, further comprising a second filament coupling the first pin to the second pin.

5. The system of claim 1, further comprising a catheter having a distal end coupled to the base.

6. The system of claim 1, further comprising one or more protrusions disposed on one or more of the plurality of arms.

7. The system of claim 6, wherein the one or more protrusions is selected from the group consisting of barbs, spikes, hooks, and tines.

8. The system of claim 6, wherein the one or more protrusions comprise a plurality of protrusions arranged in a column extending along a first of the plurality of arms and in a first plane, and a plurality of protrusions arranged in a column extending along a second of the plurality of arms and in a second plane different from the first plane.

9. The system of claim 6, wherein the protrusions extend about 0.5 millimeters to about 1.5 millimeters from one or more of the arms.

10. The system of claim 1, wherein the clamp weighs less than 0.08 grams.

11. A clamp for clamping a leaflet of a heart valve, the clamp comprising:

a body comprising:

a first arm and a second arm pivotably coupled together, the of arms having a closed configuration in which the arms are oriented toward each other, and an open configuration in which the arms are oriented away from each other;

wherein;

first ends of the arms of the clamp are configured to fixedly engage with a leaflet of the heart valve;

second ends of the arms of the clamp are pivotably coupled together to maintain the arms of the clamp in the closed configuration;

a first aperture is formed in at least one arm to facilitate coupling of the at least one arm to a spreader configured to move the clamp from the closed configuration to the open configuration; and the body is configured to be coupled to an artificial chordae tendineae.

12. The clamp of claim 11, wherein the body further comprises:

a coiled spring portion at a second end, the spring portion configured to bias the arms to the closed configuration; and a longitudinal axis extending through the first end and the second end;

wherein the clamp further comprises:

a first cover disposed adjacent to a first arm of the plurality of arms and extending along the first arm to the longitudinal axis;

a second cover disposed adjacent to a second arm of the plurality of arms and extending along the second arm to the longitudinal axis;

a pin extending through the first cover, the second cover, and the coiled spring portion;

a first channel disposed on the first cover having a central axis that is substantially parallel with the first arm; and a second channel disposed on the second cover having a central axis that is substantially parallel with the second arm.

13. The clamp of claim 12, wherein the first and second channels are configured to substantially align with second and third apertures of a spreader.

14. The clamp of claim 13, further comprising:

a first pin extending into the first channel and the second aperture;

a second pin extending through the second channel and the third aperture; and a filament coupling the first pin to the second pin.

15. The clamp of claim 11, further comprising a tab configured to transition the arms between the open configuration and the closed configuration; and wherein the open configuration and the closed configuration are each stable configurations.

* * * * *